(12) United States Patent
Lapinski et al.

(10) Patent No.: US 12,024,681 B2
(45) Date of Patent: Jul. 2, 2024

(54) PROCESS FOR INCREASING THE CONCENTRATION OF NORMAL PARAFFINS IN A LIGHT NAPHTHA STREAM

(71) Applicant: UOP LLC, Des Plaines, IL (US)

(72) Inventors: Mark Lapinski, Aurora, IL (US); Ram Ganesh Rokkam, Visakhapatnam (IN); Cora Wang Ploentham, Elk Grove Village, IL (US); Gregory Funk, Carol Stream, IL (US)

(73) Assignee: UOP LLC

( * ) Notice: Subject to any disclaimer, the term of this patent is extended or adjusted under 35 U.S.C. 154(b) by 0 days.

(21) Appl. No.: 17/859,917

(22) Filed: Jul. 7, 2022

(65) Prior Publication Data
US 2023/0036734 A1 Feb. 2, 2023

Related U.S. Application Data

(60) Provisional application No. 63/222,212, filed on Jul. 15, 2021.

(51) Int. Cl.
*C10G 35/06* (2006.01)
(52) U.S. Cl.
CPC ..... *C10G 35/06* (2013.01); *C10G 2300/1037* (2013.01)
(58) Field of Classification Search
CPC ............ C10G 35/06; C10G 2300/1037; C10G 67/06; C10G 25/03; C07C 5/2702; C07C 5/2724; C07C 7/13
See application file for complete search history.

(56) References Cited

U.S. PATENT DOCUMENTS

| | | | |
|---|---|---|---|
| 5,705,730 A * | 1/1998 | Zarchy | C07C 7/13 585/737 |
| 9,302,958 B2 * | 4/2016 | Lapinski | C10G 45/62 |
| 9,302,959 B2 * | 4/2016 | Lapinski | C10G 35/02 |
| 2005/0101814 A1 | 5/2005 | Foley | |
| 2014/0171704 A1 | 6/2014 | Erisken | |
| 2015/0315100 A1 | 11/2015 | Lapinski | |
| 2018/0327675 A1 | 11/2018 | Funk | |

OTHER PUBLICATIONS

Search Report and Written Opinion for 22185254.4 dated Feb. 9, 2023.

* cited by examiner

*Primary Examiner* — In Suk C Bullock
*Assistant Examiner* — Jason Y Chong
(74) *Attorney, Agent, or Firm* — Paschall & Associates, LLC; Mark Goldberg

(57) ABSTRACT

A process increases the concentration of normal paraffins in a feed stream comprising separating a naphtha feed stream into a normal paraffin rich stream and a non-normal paraffin rich stream. A naphtha feed stream may be separated into a normal paraffin stream and a non-normal paraffin stream. An isomerization feed stream is taken from the non-normal paraffin stream and isomerized over an isomerization catalyst to convert non-normal paraffins to normal paraffins and produce an isomerization effluent stream. The isomerization effluent stream may be separated into a propane stream and a C4+ hydrocarbon stream optionally in a single column. The C4+ hydrocarbon stream may be recycled to the step of separating a naphtha feed stream.

7 Claims, 7 Drawing Sheets

PROCESS FOR INCREASING THE CONCENTRATION OF NORMAL PARAFFINS IN A LIGHT NAPHTHA STREAM

CROSS-REFERENCE TO RELATED APPLICATIONS

This application claims priority from U.S. Provisional Application No. 63/222,212, filed Jul. 15, 2021, which is incorporated herein in its entirety.

FIELD

The field is a process for increasing the concentration of normal hydrocarbons in a feed stream.

BACKGROUND

Ethylene and propylene are important chemicals for use in the production of other useful materials, such as polyethylene and polypropylene. Polyethylene and polypropylene are two of the most common plastics found in use today and have a wide variety of uses. Uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking furnace to reduce the hydrocarbon partial pressure and enhance olefin yield as well as reducing the formation and deposition of carbonaceous material in the cracking reactors. The process is therefore often referred to as steam cracking or pyrolysis.

The composition of the feed to the steam cracking reactor affects the product distribution. The propensity of particular hydrocarbons to crack is greater than others. The tendency of the hydrocarbons to crack to ethylene normally ranks in the following order: normal paraffins; iso-paraffins: olefins; naphthenes, and aromatics. Benzene and other aromatic compounds are particularly resistant to steam cracking and undesirable as cracking feed stocks, with only the alkyl side chains being cracked to produce the desired product.

The feed to a steam cracking unit is normally a mixture of hydrocarbons varying both by type of hydrocarbon and carbon number. This variety of hydrocarbons makes it difficult to separate out less desirable feed components, such as naphthenes and aromatics, from the feed stream by fractional distillation. The normal paraffins and the non-normal paraffins can be separated by an adsorption process. Increasing the concentration of normal paraffins in a stream can improve the quality of a feedstock to the steam cracking unit.

Common feeds to steam crackers include light naphtha, which is concentrated in C5-C6 hydrocarbons, and LPG, which is mostly propane and butane as well as small concentrations of other hydrocarbons. Light naphtha streams typically contain a mixture of n-paraffins, iso-paraffins, naphthenes and aromatics. It is generally not possible to procure light naphtha streams that are concentrated in n-paraffins. Similarly, LPG streams typically contain a mixture of n-butane, iso-butane, and propane, but streams concentrated in n-butane are not commonly available.

One way to upgrade light naphtha is first to separate the naphtha into a normal paraffin rich stream and a non-normal paraffin rich stream; and subsequently convert a substantial amount of the non-normal paraffin stream in an isomerization zone in the presence of a catalyst into normal paraffins. Isomerization can produce normal butanes with the other normal paraffins which must be managed. Separating isoparaffins intended for further isomerization from normal paraffins intended for steam cracking requires a series of fractionation columns and can substantially increase capital cost.

An efficient process for separating and converting the iso-paraffins in light naphtha to normal paraffins would significantly increase the profitability of steam cracking operations by increasing the yield of high value ethylene and propylene. It has now been found that operating the first isomerization unit under specific conditions unexpectedly results in a step-change increase in the production of the desired normal paraffins both in percentage content and increasing the normal paraffin to iso-paraffin ratio.

BRIEF SUMMARY

The process increases the concentration of normal paraffins in a feed stream comprising separating a naphtha feed stream into a normal paraffin rich stream and a non-normal paraffin rich stream. An isomerization feed stream is taken from the non-normal paraffin stream and isomerized over an isomerization catalyst to convert non-normal paraffins to normal paraffins and produce an isomerization effluent stream. The isomerization effluent stream may be separated into a propane stream and a C4+ hydrocarbon stream optionally in a single column. The C4+ hydrocarbon stream may be recycled to the step of separating a naphtha feed stream. It has been found that specific changes in the conditions of the process result in a surprising and unexpected step-change increase in the production of the desired normal paraffins (C2-nC6) in the product and a sharp increase in the normal/iso-paraffin ratio in the product as compared to prior art processes.

A process is provided for increasing the concentration of normal paraffins in a feed stream comprising separating a naphtha feed stream into a normal paraffin stream and a non-normal paraffin stream wherein said non-normal paraffin stream further comprises about 1-30 wt % cyclic hydrocarbons sending said non-normal paraffin stream to be isomerized reacted over a sulfated zirconia isomerization catalyst in an isomerization zone at a temperature in a range from about 180° C. to 260° C. to convert non-normal paraffins to normal paraffins and produce an effluent stream. The process may be at a temperature is a range from about 185 to 225° C., preferably from about 185 to 215° C. The non-normal paraffin stream may be isomerized at a liquid space velocity of about 1.5 to 5.0 l/h, preferably from about 2.0-4.0 l/h. The non-normal paraffin stream may have a ratio of hydrogen/hydrocarbon of about 0.5 to 2.5 in some embodiments and 1-2.0 in other embodiments. The isomerization effluent stream may comprise a normal paraffin/methane selectivity ratio of about 40-55%. The isomerization zone maintains a pressure in the range of about 250-500 psig. The isomerization zone produces about 30-65 wt % normal paraffins.

The isomerization zone may produce about 30-60 wt % C2-C3 normal paraffins. The effluent stream may have a molecular weight ratio to non-normal paraffin stream of about 0.70 to 0.80.

The effluent stream may have a normal paraffin/iso paraffin ratio of about 0.8-1.25. The effluent stream may have a light paraffin (C2-C3) ratio to methane of about 50-60%.

In another embodiment of the invention, the cyclic hydrocarbons are first separated from the feed being sent to the isomerization zone. That process further comprises a process for increasing the concentration of normal paraffins in a feed stream comprising separating a naphtha feed stream into a normal stream and a non-normal paraffin stream comprising less than about 0.5 wt % cyclic hydrocarbons and preferably less than about 0.1 wt %

The process is in an isomerization zone and isomerizing an isomerization feed stream taken from the non-normal paraffin stream over a chlorided alumina catalyst or a sulfated zirconia catalyst isomerization catalyst at a temperature in a range from about 225 to 260° C. to convert non-normal paraffins to normal paraffins and produce an isomerization effluent stream; separating said isomerization effluent stream into a propane stream and a C4+ hydrocarbon stream.

In the process, the C4+ hydrocarbon stream is a C4-C6 hydrocarbon stream. The isomerization effluent stream may comprise a normal paraffin/methane selectivity ratio of about 40-55. The isomerization zone may maintain a pressure in the range of 450-650 psig. The isomerization zone produces about 30-65 wt % normal paraffins. The effluent stream has a light paraffins (C2-C3) over methane selectivity of about 50-60%. The isomerization effluent stream has a molecular weight ratio to said isomerization feed stream of about 0.70 to 0.80. The process is at a LHSV of about 4-7.5. The isomerization feed stream has an inlet mole ratio of H2/hydrocarbon of about 0.5 to 0.6. In another embodiment of the invention, the process is a process for treating a naphtha feed stream comprising separating a naphtha feed stream into a normal paraffin stream and a non-normal paraffin stream comprising less than about 0.5 wt/o cyclic hydrocarbons; and; in an isomerization zone isomerizing an isomerization feed stream taken from the non-normal paraffin stream over a chlorided alumina catalyst at a temperature in a range from about 225 to 260° C. to convert non-normal paraffins to normal paraffins and produce an isomerization effluent stream.

Additional details and embodiments of the invention will become apparent from the following detailed description of the invention.

DETAILED DESCRIPTION

The present disclosure endeavors to separate normal paraffins from a light naphtha stream comprising C4-C7 paraffins for an ideal steam cracker feed. The process employs a separation of normal paraffins from non-normal hydrocarbons to extract normal paraffins from the light naphtha stream and may transport these normal paraffins to a steam cracking unit. Furthermore, the non-normal hydrocarbons are converted to normal paraffins and may also be transported to a steam cracking unit. The non-normal hydrocarbons, which include iso-paraffins, naphthenes and aromatics, can optionally undergo an additional separation to separate isobutanes, isopentanes and isohexanes from the C6 cyclics and any C7+ hydrocarbons from the isopentanes and isohexanes. The isobutanes, isopentanes and isohexanes can be isomerized to increase the concentration of normal paraffins and then be subjected to separation. Mixed C4+ paraffins from isomerization can be recycled back to the normal-non-normal separation without having to separate isobutanes from normal butanes in a dedicated fractionation column. Optionally, a deisobutanizer column may separate isobutanes from C4+ paraffins and be recycled to the isomerization zone. The conditions of this invention in the first isomerization unit are set to provide significantly higher yields of normal paraffin products at a given n-paraffin/methane selectivity ratio as compared to the prior art. Examples of the conditions, testing results and comparisons to the prior art clearly show the significantly improved yield of the desired normal paraffins.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

Figure 1:
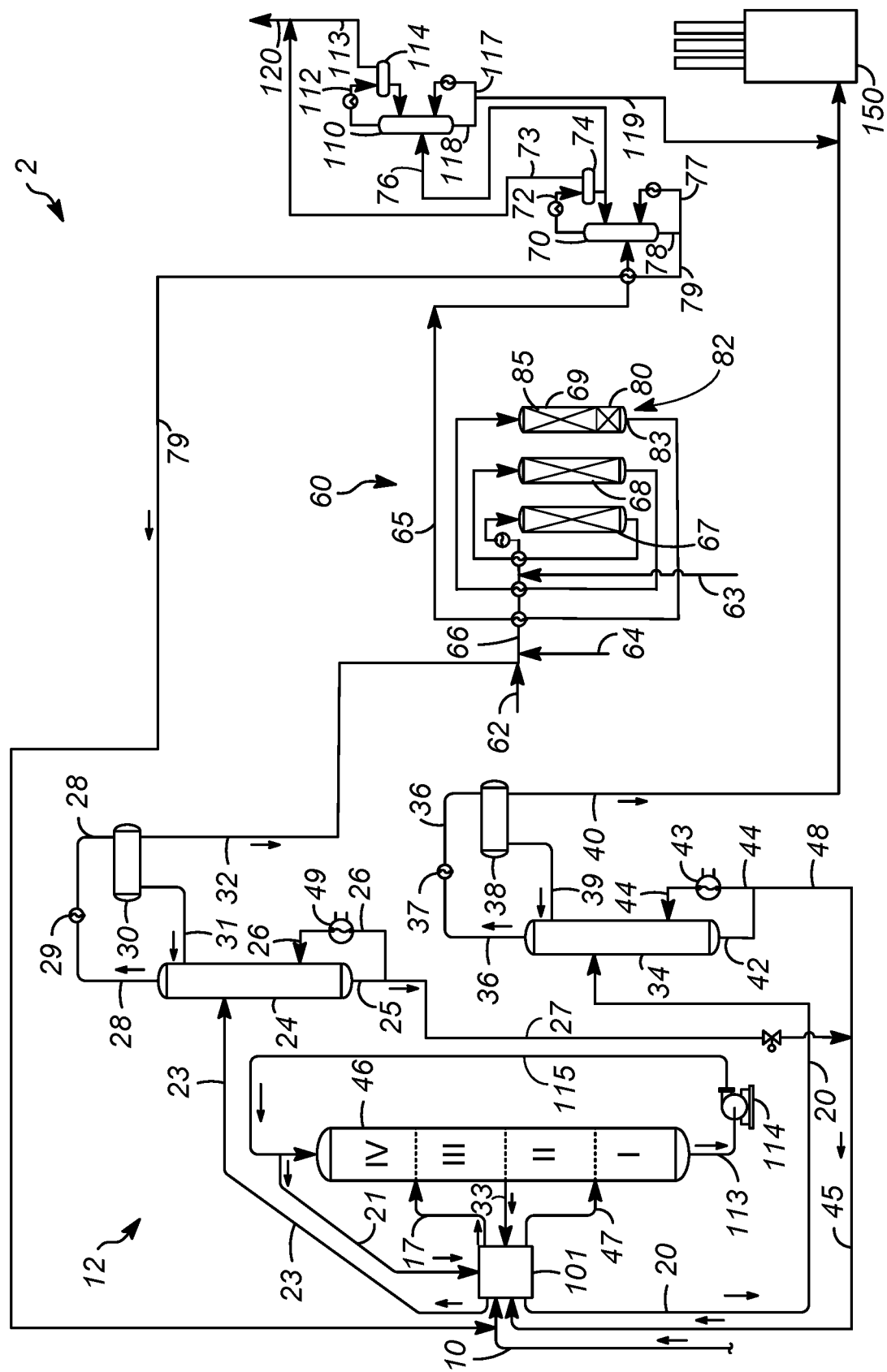
FIG. 1 is a schematic view of a conversion unit of the present disclosure.

In the process and apparatus 2 in FIG. 1, a naphtha feed stream in line 10 is preferably a hydrotreated light naphtha stream comprising substantially C4 to C6 hydrocarbons having a T90 between about 40° C. and about 90° C. The end point is taken to minimize the presence of hydrocarbons with more than six carbon atoms in the feed. Suitably no more than about 30 wt % C7+ hydrocarbons, preferably no more than about 20 wt % C7+ hydrocarbons and more preferably no more than about 10 wt % C7+ hydrocarbons can be present in the light naphtha feed stream. The naphtha feed stream may comprise normal paraffins, iso-paraffins, naphthenes, and aromatics.

It has been found that normal paraffins yield more light olefins in a steam cracking unit. Hence, it is highly desirable to increase the concentration of normal paraffins in the feed stream 10. The first step in the process is a step of separating the naphtha feed stream into a normal paraffin-rich stream and a non-normal paraffin-rich stream. Normal molecules are defined to mean straight chain molecules such as normal butane, normal hexane, and normal pentane. The most efficient process for such a separation utilizes adsorption. In an aspect, an adsorbent separation unit 12 is used to separate normal paraffins from non-normal paraffins.

As used herein, the term "a component-rich stream" or "a component stream" means that the stream coming out of a vessel has a greater concentration of the component than the feed to the vessel. As used herein, the term "a component-lean stream" means that the lean stream coming out of a vessel has a smaller concentration of the component than the feed to the vessel.

The naphtha feed stream is delivered to the process in a feed line 10 and passed to the adsorbent separation unit 12. The feed stream in feed line 10 is passed through a valve 101 in the adsorbent separation unit 12 which delivers the feed to an appropriate bed in an adsorbent vessel 46.

The feed stream in feed line 10 is separated into a normal paraffins stream and a non-normal paraffins stream. Normal paraffins of the naphtha mixture selectively enter or occlude into the porous structure of the adsorbent components but branched or cyclic non-normal chain paraffins do not typically enter the pores. The non-normal paraffins exit the process as a raffinate stream. In an aspect, the normal butanes enter or occlude into the porous structure of the adsorbent components while the non-normal butanes do not typically enter the pores in addition to the same dynamic for the C5-C7 paraffins. Consequently, the butanes are separated in the adsorbent separation unit 12 like the C5-C7 hydrocarbons.

To provide a useful method for separation of normal from non-normal paraffins, it is necessary to desorb the occluded normal paraffins. In the disclosed process, normal nonane or normal decane or even heavier normal paraffin can suitably be used as a desorbent to desorb normal paraffins in an extract-desorbent stream.

The adsorbent used in the adsorption vessel preferably comprises aluminosilicate molecular sieves having relatively uniform pore diameters of about 5 Angstroms. The preferred adsorbent is provided by commercially available type 5A molecular sieves produced and sold by UOP LLC in Des Plaines, Illinois.

The adsorbent vessel 46 may comprise a series of vertically spaced, separate beds interconnected by a pipe 115 between the bottom of one bed and the top of its upstream adjacent bed. The valve 101 may comprise a manifold arrangement or a rotary valve for advancing the points of inlet and outlet of respective streams in a downstream direction. The adsorbent vessel 46 operates in an upflow mode, although downflow may be suitable. The adsorbent vessel 46 is shown to have four beds I-IV for simplicity, but it may have more beds such as eight, twelve or twenty-four beds divided among the four main zones I-IV.

The feed stream is introduced through feed line 10 through valve 101 which is positioned to send the feed stream through line 47 into the adsorbent vessel 46 between Zones I and II. The extract is withdrawn between Zones II and III in line 33, transported through the valve 101 in an extract line 20 to an extract fractionation column 34 to separate desorbent from extract. The desorbent is introduced through desorbent line 45 through the valve 101 which is positioned to send the desorbent through a desorbent line 17 into the process between Zones III and IV. The raffinate is withdrawn between Zones IV and I through a raffinate line 21, through the valve 101 and through line 23 to the raffinate fractionation column 24.

Simulated countercurrent flow is achieved by periodically advancing downstream the introduction point of the feed stream and the desorbent stream while simultaneously and equally advancing downstream the withdrawal point of the raffinate stream and the extract stream. The Zone I is defined as the zone bounded between the feed stream inlet and the raffinate outlet; the Zone II is defined as the zone bounded between the extract stream outlet and the desorbent inlet; the Zone III is defined as the zone bounded between the desorbent inlet and the extract outlet; and the Zone IV is defined as the zone bounded between the raffinate stream outlet and the desorbent stream inlet. Typical liquid phase operation is preferred, for example, at temperatures from about 50° C. to about 300° C., and more particularly no more than about 260° C., and pressures from slightly superatmospheric to about 30 atmospheres.

Raffinate, characterized as comprising molecules less adsorbed in the adsorbent vessel 46, is withdrawn from the adsorbent vessel 46 in the raffinate line 21 through the valve 101 and enters the raffinate fractionation column 24 through line 23. Since it is desired to obtain a normal paraffin product, the raffinate fractionation column 24 is operated to separate two fractions, a raffinate overhead stream rich in non-normal paraffins, in an embodiment, rich in C7− non-normal paraffins, and a desorbent bottoms stream rich in normal paraffin desorbent, in an embodiment, rich in C9+ normal paraffins. The raffinate overhead stream is withdrawn from the raffinate fractionation column 24 in an overhead line 28, condensed in a cooler 29 and fed to a separator 30. A portion of the condensed raffinate overhead is recycled to the raffinate fractionation column 24 as reflux through a reflux line 31 and the remaining portion of the condensed raffinate overhead is withdrawn through a net raffinate overhead line 32. The net raffinate overhead stream is rich in non-normal C7− paraffins which can be transported to the isomerization unit 60 as the non-normal paraffin rich stream. Alternatively, the net raffinate overhead stream in the overhead line 28 may be fully condensed and fully refluxed in line 31 and the non-normal paraffin rich stream can be taken in a side cut from the raffinate column 24.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

The raffinate bottoms stream is withdrawn from the raffinate fractionation column 24 through a bottoms line 25 where a portion of the raffinate bottoms stream flows through a reboiler line 26, reboiler heater 49 and returns heated to the raffinate fractionation column 24. The remaining portion of said raffinate bottoms stream flows through a net bottoms line 27 as a normal paraffin rich stream, particularly rich in normal C9+ paraffins. The raffinate bottoms stream comprising a raffinate desorbent stream in line 27 can be recycled to the adsorption vessel 46 in the desorbent line 45 perhaps after joining an extract bottoms stream in line 48. The raffinate fractionation column 24 operates in a bottoms temperature range of about 250 to about 290° C. and an overhead pressure of about 450 to about 550 kPa (gauge).

Extract comprises molecules more selectively adsorbed on the adsorbent vessel 46. The desorbent displaces the selectively adsorbed normal paraffins from the solid adsorbent in desorbent bed III of adsorbent vessel 46. The extract and desorbent are withdrawn in line 33, and the valve 101 connects line 33 with line 20. Extract and desorbent withdrawn from the adsorbent vessel in the extract line 33 connected through the valve 101 is directed in line 20 to the extract fractionation column 34. Since it is desired to obtain a normal paraffin product, the extract fractionation column 34 is operated to separate two fractions, an extract overhead stream rich in normal paraffins, in an embodiment, rich in C4-C7 normal paraffins, and a desorbent bottoms stream rich in normal paraffin desorbent, in an embodiment, rich in C9+ normal paraffins. The extract overhead stream is withdrawn from the extract fractionation column 34 in an overhead line 36, condensed in a cooler 37 and fed to a separator 38. A portion of the condensed extract overhead stream is recycled to the extract fractionation column 34 as reflux through a reflux line 39 and the remaining portion of the condensed extract overhead stream is withdrawn through a net extract overhead line 40. The extract overhead stream is rich in C4-C7 normal paraffins which can be recovered or taken as steam cracker feed and fed to the steam cracker unit 150 in line 40.

The extract bottoms stream is withdrawn from extract fractionation column 34 through a bottoms line 42 where a portion of the extract bottoms stream flows through a reboiler line 44, reboiler heater 43 and returns heated to the extract fractionation column 34. A remaining portion of the extract bottoms stream flows through line 48 as a normal paraffin rich stream, particularly rich in normal C9+ paraffins. The extract bottoms stream in line 48 comprising an extract desorbent stream can join the raffinate bottoms stream in line 27 comprising a raffinate desorbent stream. Both can be recycled in the desorbent line 45 through the valve 101 to the adsorbent vessel 46 in the desorbent line 17. The extract fractionation column 34 operates in bottoms temperature range of about 225 to about 275° C. and an overhead pressure of about 250 to about 350 kPa (gauge).

The non-normal paraffin rich stream particularly rich in non-normal C4 to C7 paraffins which may be taken in the net raffinate overhead stream in the net raffinate overhead line 32 can be isomerized to increase the concentration of normal C4 to C7 paraffins to equilibrium levels. In one embodiment, the non-normal paraffin rich stream may be fractionated by a debutanizer column (not shown) into a C4 stream that is taken as the isomerization feed stream in which case some or all of the C5-C7 non-normal paraffins may be taken as an additional isomerization stream that is separately isomerized in an additional isomerization reactor to improve normal paraffin concentration. In another embodiment, the non-normal paraffin rich stream may be fractionated in a depentanizer column into a C4-C5 stream that is taken as the isomerization feed stream in which case some or all of the C6-C7 non-normal paraffins may be taken as the additional isomerization stream that is separately isomerized in the additional isomerization reactor to improve normal paraffin concentration. In another embodiment, the non-normal paraffin rich stream may be fractionated in a raffinate splitter column into a C4-C6 stream that is taken as the isomerization feed stream or separate a C4 stream that is isomerized in a first isomerization unit and a C5-C6 stream that is isomerized in a higher isomerization unit. In such an embodiment, the raffinate splitter column may be employed to remove C6 cyclic hydrocarbons, such as cyclohexane, methylcyclopentane and benzene, and C7 non-normal paraffins in a net splitter bottoms stream that can be taken to a reforming unit to produce aromatic hydrocarbons or sent to the steam cracker 150. In a further embodiment, the entire non-normal paraffin rich stream particularly rich in non-normal C4 to C7 paraffins may be taken as isomerization feed stream.

We have discovered that the conversion of non-normal hydrocarbons to normal paraffins in an isomerization unit 60 can be increased by increasing the isomerization temperature. Specifically, by increasing the temperature disproportionation reactions occur which lead to increased amounts of valuable propane and butanes, as well as increases in the per pass conversion of the iso-paraffin hydrocarbons in the feed to normal paraffins. The products from the disproportionation reactions undergo isomerization reactions leading to an increase in yields of normal paraffins. Furthermore, additional conversion to C2 to C4 normal paraffins in the non-normal paraffin rich stream is accomplished via hydrocracking reactions in the isomerization unit 60. We have surprisingly found that naphthenes and aromatics fed to the isomerization unit 60 under the more severe conditions will not significantly inhibit disproportionation reactions and will undergo ring opening and be converted to n-paraffins. Accordingly, FIG. 1 will depict the embodiment in which the non-normal paraffin rich stream rich in C4-C7 non-normal paraffins is taken from the net raffinate overhead stream in the net raffinate overhead line 32 as the isomerization feed stream without any intermediate separation between the raffinate column 24, other than in the separator 30, and the isomerization unit 60. The isomerization unit 60 may be in downstream communication with the adsorption unit 12.

The non-normal paraffin rich stream in the net raffinate overhead line 32 may be combined optionally with a fresh isobutane stream in a fresh isobutane line 62 and with a hydrogen stream in a hydrogen line 64 to provide an isomerization feed stream in an isomerization feed line 66.

In the isomerization unit 60, isoparaffins and non-normal hydrocarbons in the presence of hydrogen provided by hydrogen line 64 and an isomerization catalyst are converted to increase the concentration of normal paraffins: ethane, propane, normal butane, normal pentane and normal hexane. Four reactions promote the production of normal paraffins from iso-paraffins: disproportionation reactions, ring opening of aromatics, via preliminary saturation, and cyclics, reverse isomerization of iso-paraffins, and paraffin hydrocracking reactions.

The conversion of isopentane and/or isohexane increases significantly via disproportionation reactions due to the higher temperature in the isomerization reactors 67-69. It is believed that the paraffin disproportionation reactions occur by the combination of two iso-paraffins followed by scission into one lighter hydrocarbon and one heavier hydrocarbon. For example, two isopentanes can combine and form an isobutane and an isohexane in the presence of hydrogen. The isobutanes can further react via disproportionation to form propanes and isopentanes. A portion of the produced isobutanes can also convert to normal butanes via isomerization reactions in the isomerization unit. Production of normal propane and butane via disproportionation and isomerization reactions occurs with low production of low-value undesired methane as a cracked product. Thus, there is an increase in the overall yield of the normal paraffins in the first isomerization unit 60.

In the isomerization unit 60, hydrocracking of the isopentane and/or isohexane occurs to produce methane, ethane, propane, and isobutane. The isobutane can further react via disproportionation reactions and/or isomerization reactions to further produce normal paraffins.

It has further been found that operation of the isomerization zone at specific conditions results in a surprising and unexpected step-change increase in the resulting amount of C2 to nC6 normal paraffins in the product and a significant increase in the product normal to isoparaffin ratio as compared to the prior art. In one embodiment, the conditions include temperatures over about 204° C., LHSV over about 2.0 h−1, and H2/HC inlet mole ratios greater than about 0.32. More preferred conditions are temperatures over about 225C, LHSV over about 4 h−1 and H2/HC inlet mole ratios greater than about 0.5. It was found that these conditions were appropriate when using a chlorinated alumina catalyst. In additional experiments, it was found that a sulfated zirconia catalyst could also be used under somewhat different conditions including temperatures greater than about 180C, pressure in the range of 250-500 psig, H2/HC of about 0.6 to 2.3 mol/mol and LHSV 3-12 h−1. With higher per-pass conversions to normal paraffins, the amount of isoparaffin recycle is decreased leading to reduced capital and operating expense for the separation and conversion units.

Furthermore, there is provided a high yield of C2 to nC6 normal paraffins while maintaining a normal paraffin/methane selectivity ratio of at least about 50. Methane is an undesired product for the steam cracker. When compared to the prior art, the invention provides a significantly higher yield of normal paraffin products at a given n-paraffin/methane selectivity ratio. With higher per-pass conversions to normal paraffins, the amount of isoparaffin recycle is decreased leading to reduced capital and operating expenses for the separation and conversion units.

The process increases the concentration of normal paraffins in a feed stream comprising separating a naphtha feed stream in an adsorbent unit into a normal paraffin rich stream and a non-normal paraffin rich stream. The normal paraffin rich stream may be fed to a steam cracker. The non-normal paraffin rich stream is passed over a first isomerization catalyst to convert non-normal paraffins to normal paraffins and produce a first isomerization effluent stream. An iso-C4 stream is separated from the first isomerization effluent stream and isomerized over a second isomerization catalyst to convert iso-C4 hydrocarbons to normal C4 hydrocarbons and produce a second isomerization effluent stream. The second isomerization effluent stream may be fed to a steam cracker.

Alternatively, after separating a naphtha feed stream into a normal paraffin rich stream and a non-normal paraffin rich stream, the process comprises separating the non-normal paraffin rich stream to provide an iso-C6 paraffin rich stream and a methylcyclopentane or C6 cyclic rich stream; and passing the iso-C6 paraffin rich stream over a first isomerization catalyst to convert non-normal paraffins to normal paraffins and produce an isomerization effluent stream. The conditions in the first isomerization unit are set to provide significantly higher yields of normal paraffin products at a given n-paraffin/methane selectivity ratio as compared to the prior art. The below examples contain the conditions, testing results, and plots and clearly shows the surprising performance of the invention versus the prior art.

In an embodiment, the process may include a raffinate splitter column 50 downstream of the adsorbent separation vessel 46 to separate the net raffinate overhead stream comprising non-normal paraffins in line 32 into an isobutane stream and an isopentane stream. The isopentane stream may also be rich in isohexane and be an isohexane stream. The isopentane and/or isohexane stream may be characterized as a higher isoalkane stream. The net raffinate overhead stream comprising non-normal paraffins in line 32 may also be separated into a C6 cyclic and C7+ hydrocarbons stream in the raffinate splitter column 50. Since the non-normal paraffin stream in line 32 contains little n-hexane with a normal boiling point of 69° C. because it is removed in the adsorption separation vessel 46, the separation of C6 cyclics from iso-paraffins is simplified. The lightest C6 cyclic hydrocarbon is methylcyclopentane having a normal boiling point of 72° C. whereas iso-C6 paraffins normally boil at 50-64° C. Hence, the proper ordering of separation steps obviates a difficult split between normal hexane and methylcyclopentane that would be capitally and operationally intensive and result in a loss of much of the normal hexane, which is a valuable steam cracker feed.

The raffinate splitter overhead stream in the raffinate splitter net overhead line 56 separated from the non-normal paraffin stream in line 32 is rich in isobutanes and can be termed an isobutane stream. The isobutane stream is withdrawn in a raffinate splitter overhead line 52 from an overhead of the raffinate splitter column 50 and passed through a cooler 53 and into a separator 54. A portion of the raffinate splitter overhead stream is recycled to the raffinate splitter column 50 as reflux through a reflux line and the remaining portion of the raffinate splitter overhead stream is withdrawn in a net raffinate splitter overhead line 56. The raffinate splitter overhead stream is rich in isobutane. The isobutane stream taken in the net raffinate splitter overhead line 56 from the non-normal paraffin stream in line 32 may be charged as a first isomerization feed stream to a first isomerization unit 80 to increase its normal-butane concentration.

The raffinate splitter side stream taken in an intermediate line 58 may be rich in isopentanes and can be termed as an isopentane stream. The raffinate splitter side stream taken in an intermediate line 58 may also be rich in isohexanes and be termed as an isohexane stream. The raffinate splitter side stream can be termed a higher isoalkane stream because it is rich in isopentane and/or isohexane. The raffinate splitter side stream comprising higher isoalkanes is withdrawn from a side 51 of the raffinate splitter column 50 in the intermediate line 58. The higher isoalkane stream may be taken in the intermediate line from the side 51 of the raffinate splitter column 50 from the non-normal paraffin stream in the net raffinate overhead line 32 and fed as a second, higher isoalkane isomerization feed stream to a second, higher isomerization unit 60 to increase its normal alkane concentration. Particularly, the higher isomerization unit 60 increases the concentration of normal pentanes and/or normal hexanes.

The raffinate splitter bottoms stream is withdrawn from raffinate splitter column 50 through a bottoms line 55 from which a portion of the raffinate splitter bottoms flows through a reboiler line 59, a reboiler heater 57 and returns to the raffinate splitter column 50. The remaining portion of the raffinate splitter bottoms stream flows through a net splitter bottoms line 64 as a cyclic hydrocarbon stream rich in cyclic C6 hydrocarbons and benzene and particularly rich in methylcyclopentane. The cyclic paraffins stream in the net splitter bottoms line 64 can be taken to a reforming unit to produce aromatic hydrocarbons or sent to the steam cracker 150. Any C4+ hydrocarbons produced from steam cracking or reforming the cyclic paraffins stream can be recycled to the adsorption separation unit 12. The raffinate splitter column 50 operates in bottoms temperature range of about 124 to about 154° C. and an overhead pressure range of about 0 to about 138 kPa (gauge).

The isobutane stream in the net raffinate splitter overhead line 56 may be combined with a first hydrogen stream in a first hydrogen line 82 and optionally a fresh isobutane stream in a fresh isobutane line 81 to provide an isobutane isomerization feed stream in an isobutane isomerization feed line 84. The isobutane isomerization feed stream is heated by heat exchange with an isobutane isomerization effluent stream and isomerized in a first, butane isomerization unit 80. In the butane isomerization unit 80, the isobutane paraffins, in the presence of hydrogen provided by the hydrogen line 83 and a butane isomerization catalyst, are converted into normal butane to attain equilibrium levels of normal butane.

In addition to isobutane-normal butane isomerization, the conversion of isobutane via disproportionation reactions can also occur. The isobutanes can react via disproportionation to form propane and a pentane. The isopentanes can also isomerize to equilibrium producing normal pentane. Thus, there is an increase in the overall yield of the normal paraffins to propane, normal butane and normal pentane in the butane isomerization unit 80.

The butane isomerization catalyst in the butane isomerization unit 80 may include chlorided alumina, sulfated zirconia, tungstated zirconia or zeolite-containing isomerization catalysts. The butane isomerization catalyst may be amorphous, e.g., based upon amorphous alumina, or zeolitic. A zeolitic catalyst would still normally contain an amorphous binder. The butane isomerization catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the butane isomerization unit 80. If chlorided alumina catalyst is used as the butane isomerization catalyst, a chloriding agent in line 83 will be added to the butane isomerization feed stream 84.

The butane isomerization conditions in the butane isomerization unit 80 include reactor temperatures ranging from about 40° C. to about 250° C., preferably at reactor temperatures ranging from 90° C. to 230° C. Reactor operating pressures generally range from about 100 kPa to 10 MPa absolute. Liquid space velocity ranges from about 0.2 to about 25 volumes of hydrocarbon feed per hour per volume of catalyst. Hydrogen is admixed with the butane isomerization feed to the butane isomerization unit 80 to provide a mole ratio of hydrogen to hydrocarbon feed of from about 0.01 to 20. The hydrogen may be supplied totally from outside the process or supplemented by hydrogen recycled to the feed after separation from the butane isomerization reactor effluent.

Contacting within the butane isomerization unit 80 may be made using the catalyst in a fixed-bed system, a moving-bed system, a fluidized-bed system, or in a batch-type operation. The reactants may be contacted with the bed of catalyst particles in upward, downward, or radial-flow fashion. The reactants may be in the liquid phase, a mixed liquid-vapor phase, or a vapor phase when contacted with the catalyst particles, with a mixed phase or vapor phase being preferred. The butane isomerization unit 80 may be in a single reactor 86 or two or more separate reactors 86 and 88 with suitable means therebetween to ensure that the desired isomerization temperature is maintained at the entrance to each zone. Even though the main reaction in the butane isomerization unit is isomerization of isoparaffins to normal paraffins which is endothermic, sufficient exothermic hydrogenation reactions occur causing the temperatures across the reactors to increase. Consequently, the butane isomerization effluent from an upstream reactor 86 must be cooled before going to a downstream reactor 88. For example, a first butane isomerate stream from a first butane isomerization reactor 86 may be cooled by heat exchange with the butane isomerization feed stream in line 84 and fed to a second butane isomerization reactor 88. Moreover, a second butane isomerate stream from the second butane isomerization reactor 88 may be heat exchanged with the butane isomerization feed stream comprising an isobutane-rich stream mixed with hydrogen to cool the second butane isomerate and cool the butane isomerization feed stream upstream of the heat exchange with the first butane isomerate stream. Two or more reactors in sequence enable improved isomerization through control of individual reactor temperatures and partial catalyst replacement without a process shutdown. A first, butane isomerization effluent stream comprising an increased concentration of normal paraffins exits the last reactor in the butane isomerization unit 80 in a butane isomerization effluent line 90. The butane isomerization effluent stream in line 90 may be fed to a depropanizer column 70 in a depropanizer feed line 92 after it is combined with a second isomerization effluent stream in line 65.

The non-normal, non-cyclic paraffin rich stream in the intermediate raffinate splitter line 58 may be combined with a hydrogen stream in a higher hydrogen line 62 and heated by heat exchange with reactor effluent and fed to a higher isomerization unit 60. In the higher isomerization unit 60, isopentane and/or isohexane, in the presence of hydrogen provided by hydrogen line 62 and a higher isomerization catalyst, are converted to increase the concentration of normal paraffins: ethane, propane, normal butane, normal pentane and normal hexane. Three reactions promote the production of normal paraffin-iso-paraffin disproportionation reactions, opening of aromatics and cyclics, reverse isomerization of iso-paraffins, and paraffin hydrocracking reactions.

Cracking of some of the paraffins can occur in the higher isomerization unit 60 to produce C4– paraffins. Moreover, the conversion of isopentane and/or isohexane increases significantly via disproportionation reactions because the non-normal, non-cyclic paraffin rich stream in the intermediate raffinate splitter line 56 is passed into the higher isomerization unit 60 lean in cyclic C6 hydrocarbons. It is believed that the paraffin disproportionation reactions occur by the combination of two iso-paraffins followed by scission into one lighter hydrocarbon and one heavier hydrocarbon. For example, two isopentanes can combine and form an isobutane and an isohexane in the presence of hydrogen. The isobutanes can further react via disproportionation to form a propanes and isopentanes. A portion of the produced isobutanes also converts to normal butanes via isomerization reactions in the isomerization zone. Production of normal propane and butane via disproportionation and isomerization reactions occurs with low production of low-value undesired methane as a cracked product. Thus, there is an increase in the overall yield of the normal paraffins in the first isomerization unit 60.

In the higher isomerization unit 60, hydrocracking of the isopentane and/or isohexane occurs to produce methane, ethane, propane, and isobutane. The isobutane can further react via disproportionation reactions and/or isomerization to further produce normal paraffins.

The higher isomerization catalyst in the higher isomerization unit 60 may include chlorided alumina, sulfated zirconia, tungstated zirconia or zeolite-containing isomerization catalysts. The higher isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the isomerization unit 60. If a chlorided alumina catalyst is used as the isomerization catalyst, a chloriding agent in line 63 will be added to the higher isomerization feed stream 61. In the examples herein, the catalysts that are used are chloride alumina or sulfated zirconia catalysts.

The higher isomerization process conditions in the higher isomerization unit 60 include an average reactor temperature usually ranging from about 1800 to about 210° C. Reactor operating pressures generally range from about 250 to 500 psig. Liquid hourly space velocities (LHSV) range from about 3 to about 12 volumes of hydrocarbon feed per hour per volume of catalyst. Hydrogen is admixed with or remains with the higher isomerization feed to the higher isomerization unit to provide a mole ratio of hydrogen to hydrocarbon feed of from about 0.6 to 2.3. The hydrogen may be supplied totally from outside the process or supplemented by hydrogen recycled to the feed after separation from higher isomerization reactor effluent.

Contacting within the higher isomerization unit 60 may be made using the higher isomerization catalyst in a fixed-bed system, a moving-bed system, a fluidized-bed system, or in a batch-type operation. The reactants may be contacted with the bed of higher isomerization catalyst particles in upward, downward, or radial-flow fashion. The reactants may be in the liquid phase, a mixed liquid-vapor phase, or a vapor phase when contacted with the higher isomerization catalyst particles, with a mixed phase or vapor phase being preferred. The higher isomerization unit 60 may be in a single reactor 66 or in two or more separate higher isomerization reactors 67, 68, and 69 with suitable means therebetween to ensure that the desired isomerization temperature is maintained at the entrance to each reactor.

The reactions in the higher isomerization unit 60 generate an exotherm across the reactors so the higher isomerization effluent streams need to be cooled between reactors. For example, a first higher isomerate stream from a first isomerization reactor 67 may be heat exchanged with the higher isomerization feed stream in the higher isomerization feed line 61 comprising the non-normal, non-cyclic paraffin rich stream mixed with hydrogen to cool the higher isomerate and heat the higher isomerization feed stream. Moreover, a second higher isomerate stream from a second higher isomerization reactor 68 may be heat exchanged with the higher isomerization feed stream comprising the non-normal, non-cyclic paraffin rich stream mixed with hydrogen upstream of the heat exchange with the first higher isomerate steam to cool the higher isomerate stream and heat the higher isomerization feed stream. Additionally, a third isomerate stream from the third isomerization reactor 69 may be heat exchanged with the higher isomerization feed stream comprising non-normal, non-cyclic paraffin rich stream mixed with hydrogen upstream of the heat exchange with the second higher isomerate stream to cool the higher isomerate and heat the higher isomerization feed stream. Since hydrocracking reactions are accompanied by hydrogenation reactions that are very exothermic, two to five higher isomerization reactors in sequence enable improved control of individual reactor temperatures and partial catalyst replacement without a process shutdown. A higher isomerization effluent stream comprising an increased concentration of normal paraffins exits the last higher isomerization reactor 69 in the higher isomerization unit 60 in a higher isomerization effluent line 65.

A depropanizer column 70 separates a higher isomerization effluent stream in line 65 into a depropanizer overhead stream comprising propane and a depropanized bottoms stream comprising C4+ paraffins in a single fractionation column. In an embodiment, a depropanizer column 70 separates the higher isomerization effluent stream in line 65 and a butane isomerization effluent stream in line 90 into a depropanizer overhead stream comprising propane and a depropanized bottoms stream comprising C4+ paraffins in a single fractionation column. Line 92 may take the higher isomerization effluent stream in line 65 and a butane isomerization effluent stream in line 90 and feed them to the depropanizer column 70 as a combined depropanizer feed stream.

A depropanizer overhead stream is withdrawn from the depropanizer column 70 in a depropanizer overhead line 72 and condensed in a cooler and passed into a separator 74. A portion of the condensed depropanizer overhead stream is recycled to the depropanizer column 70 as reflux through a reflux line and the remaining portion of the condensed depropanizer overhead stream is withdrawn in a net depropanizer overhead line 76 as a propane stream. The propane stream in the line 76 may be charged as feed to the steam cracker 150 or to a paraffin dehydrogenation process (not shown) perhaps after separation of lighter components from the propane. A depropanizer off gas stream comprising C2– hydrocarbons and light gases is taken from the separator overhead in a depropanizer off-gas line 73. The depropanizer off gas in the off-gas overhead line 73 may be scrubbed (not shown) to remove chlorine if a chloride isomerization catalyst is in the butane isomerization unit 80 or the higher isomerization unit 60 and passed to fuel gas processing or sent to further processing for further recovery of hydrogen and/or ethane which can be used as steam cracking feed to the steam cracking unit 150.

The depropanized bottoms stream is withdrawn from the depropanizer column 70 through a bottoms line 78 from which a portion of the depropanized bottoms stream flows through a reboiler line 77, a reboiler heater and returns to the depropanizer column 70. The remaining portion of the depropanized bottoms flows through a net depropanized bottoms line 79 rich in C4-C7 normal and iso-paraffins, is cooled by heat exchange with the depropanizer feed stream in line 92 and is recycled to the feed line 10 to the adsorption separation unit 12 for separation of the normal paraffins from the non-normal paraffins. The C4-C7 hydrocarbon stream may be characterized as a C4+ hydrocarbon stream. In an embodiment, the entire C4-C7 paraffin stream is recycled to the adsorption separation unit 12. The depropanizer column 70 operates in bottoms temperature range of about 90 to about 150° C. and an overhead pressure range of about 1.3 to about 2.7 MPa and preferably about 1.7 to about 2.5 MPa. The recycle line 79 may be in downstream communication with the saturation bed reactor 80. Moreover, the adsorbent vessel 46 may be in downstream communication with the recycle line 79

Because the complete depropanized bottoms stream comprising C4+ hydrocarbons, specifically C4-C7 hydrocarbons, can be recycled to the adsorption separation unit 12, without having to separate normal butanes from iso-butanes in a dedicated deisobutanizer column, the process and apparatus 2 is much simplified.

In an embodiment, the propane stream in the net depropanizer overhead line 76 may be passed to a deethanizer column 110 to remove lighter materials from the propane stream before it is fed to the steam cracker 150 or subjected to paraffin dehydrogenation. The deethanizer column 110 separates the propane stream in line 76 into a deethanizer overhead stream comprising ethane and lighter materials and a deethanized propane bottoms stream comprising C3 paraffins in a single fractionation column.

A deethanizer overhead stream is withdrawn from the deethanizer column 110 in a deethanizer overhead line 112 and condensed in a cooler and passed into a separator 114. A condensed deethanizer overhead stream is recycled to the deethanizer column 110 as reflux through a reflux line. A net vaporous deethanizer overhead stream is withdrawn in a net deethanizer overhead line 113 as an ethane stream. The ethane stream in the deethanizer overhead line 113 may be joined by the depropanizer off gas stream comprising C2– hydrocarbons and light gases in the depropanizer off-gas line 73 to provide a mixed ethane stream in an ethane line 120. The mixed ethane stream in the line 120 may be charged as feed to the steam cracker 150 as is or further demethanized (not shown) to isolate a purer ethane stream for feed to the steam cracker while the demethanized overhead may be passed to fuel gas processing or sent to further processing for further recovery of hydrogen. The mixed ethane stream in the ethane line 120 may also be scrubbed (not shown) to remove chlorine if a chloride isomerization catalyst is in the butane isomerization unit 80 or the higher isomerization unit 60.

A deethanized propane stream is withdrawn from the deethanizer column 110 through a bottoms line 118 from which a portion of the deethanized propane stream flows through a reboiler line 117, a reboiler heater and returns to the deethanizer column 110. The remaining portion of the deethanized propane stream flows through a net deethanized bottoms line 119. The deethanized propane stream may be fed to the stream cracker 150, perhaps in line 40. The deethanizer column 110 operates in bottoms temperature range of about 100 to about 130° C. and an overhead pressure range of about 1.5 to about 3 MPa (gauge).

Figure 2:
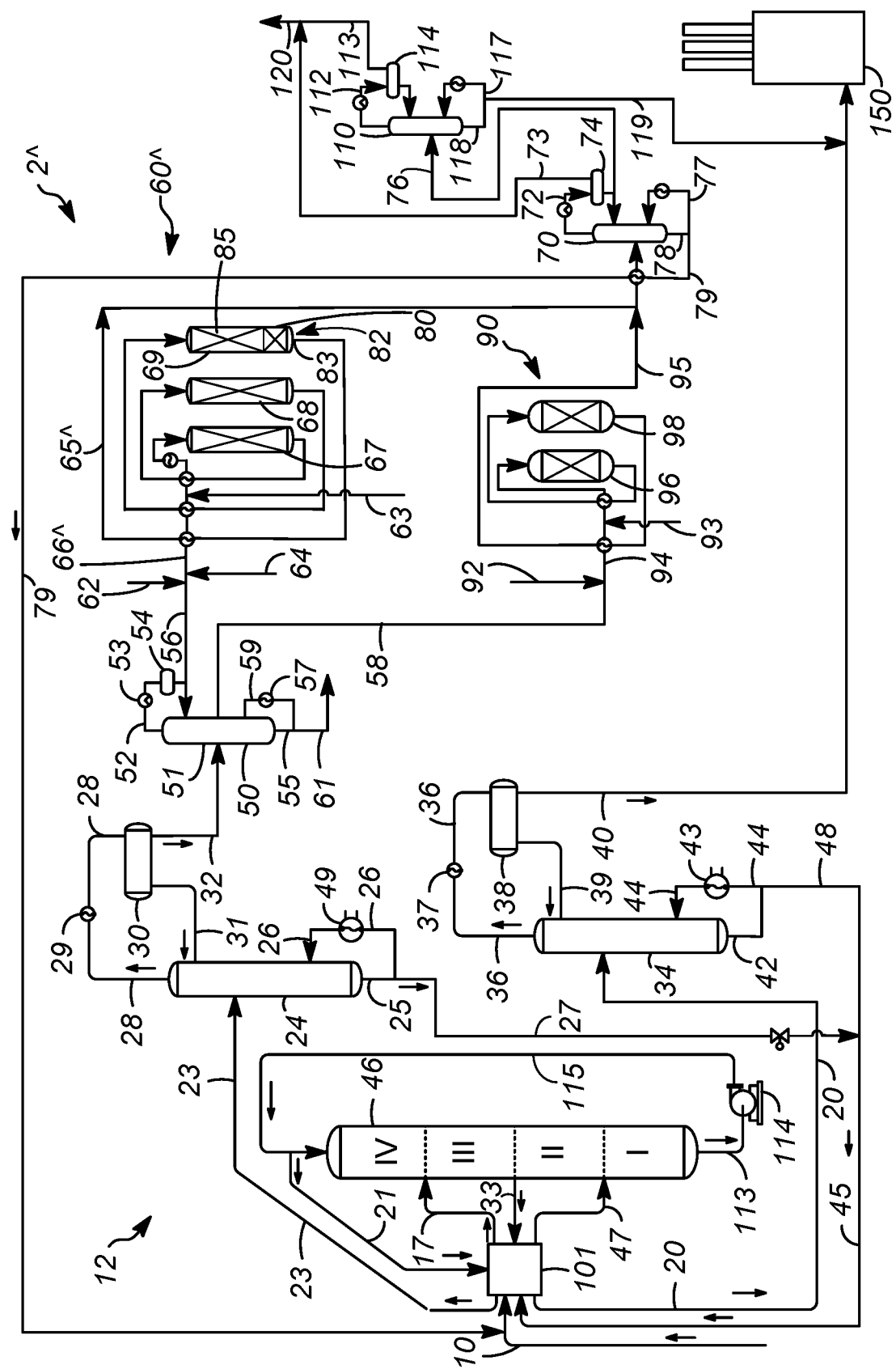
FIG. 2 is a schematic view of an alternate conversion unit of FIG. 1.

FIG. 2 shows an embodiment of a process and apparatus 2' which utilizes a single isomerization unit 60' in the isomerization zone 100'. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1.

In the alternative embodiment of FIG. 2, the process 2' installs an optional raffinate splitter column 50' downstream of the adsorbent separation vessel 46 to separate the net raffinate overhead stream comprising non-normal paraffins in line 32' into a raffinate splitter overhead stream that is rich in isobutanes comprising an isobutane stream and a bottoms stream rich in C6 cyclics and comprise a C6 cyclics and C7+ hydrocarbon stream. A control valve on line 32' admits the net raffinate overhead stream into the raffinate splitter column 50'. The raffinate splitter overhead stream may be rich in isopentane and may comprise an isopentane stream. The raffinate splitter overhead stream may also be rich in isohexane and may comprise an isohexane stream. The raffinate splitter overhead stream may be characterized as an isoalkane stream. The net raffinate overhead stream comprising non-normal paraffins in line 32' may also be separated into a C6 cyclic and C7+ hydrocarbons stream in the raffinate splitter column 50'. Since the non-normal paraffin stream in line 32' contains little n-hexane with a normal boiling point of 69° C. because it is removed in the adsorption separation vessel 46, the separation of C6 cyclics from iso-paraffins is simplified. The lightest C6 cyclic hydrocarbon is methylcyclopentane having a normal boiling point of 72° C. whereas iso-C6 paraffins normally boil at 50-64° C. Hence, the proper ordering of separation steps obviates a difficult split between normal hexane and methylcyclopentane that would be capital and operationally intensive and result in a loss of much of the normal hexane, which is a valuable steam cracker feed.

The raffinate splitter overhead stream in the raffinate splitter net overhead line 52 separated from the non-normal paraffin stream in line 32' is rich in isobutanes, isopentanes and/or isohexanes. The raffinate splitter overhead stream is withdrawn in a raffinate splitter overhead line 52 from an overhead of the raffinate splitter column 50' and passed through a cooler 53 and into a separator 54. A portion of the raffinate splitter overhead stream is recycled to the raffinate splitter column 50' as reflux through a reflux line and the remaining portion of the raffinate splitter overhead stream is withdrawn in a net raffinate splitter overhead line 56'. The raffinate splitter overhead stream taken in the net raffinate splitter overhead line 56' from the non-normal paraffin stream in line 32' may be charged as a first and perhaps only isomerization feed stream to an isomerization unit 60' to increase its normal-alkane concentration.

The raffinate splitter bottoms stream is withdrawn from raffinate splitter column 50' through a bottoms line 55 from which a portion of the raffinate splitter bottoms flows through a reboiler line 59, a reboiler heater 57 and returns to the raffinate splitter column 50'. The remaining portion of the raffinate splitter bottoms stream flows through a net splitter bottoms line 64 as a cyclic hydrocarbon stream rich in cyclic C6 hydrocarbons and benzene and particularly rich in methylcyclopentane. The cyclic paraffins stream in the net splitter bottoms line 64 can be taken to a reforming unit to produce aromatic hydrocarbons or sent to the steam cracker 150. Any C4+ hydrocarbons produced from steam cracking or reforming the cyclic paraffins stream can be recycled to the adsorption separation unit 12. The raffinate splitter column 50 operates in bottoms temperature range of about 124 to about 154° C. and an overhead pressure range of about 0 to about 138 kPa (gauge).

It should also be noted that in a further embodiment, a control valve on line 32' can be shut and a control valve on a bypass line 94 be opened to bypass the raffinate splitter column 50' in the bypass line to permit some or the entire non-normal stream in the net raffinate line 32' to enter the single isomerization unit 60' without removing C6 cyclics and C7+ hydrocarbons from the single isomerization feed stream in line 62 in the event that the single isomerization catalyst can catalyze sufficient isomerization to normal C4-C6 paraffins.

The non-normal, non-cyclic paraffin rich stream in the raffinate splitter net overhead line 56' and/or the non-normal stream from the net raffinate line 32' and bypassed in bypass line 94 may be combined with a hydrogen stream in a hydrogen line 62 and heated by heat exchange with reactor effluent and fed to a single isomerization unit 60'. In the single isomerization unit 60', isobutane, isopentane and/or isohexane, in the presence of hydrogen provided by hydrogen line 62 and an isomerization catalyst, are converted to increase the concentration of normal paraffins: ethane, propane, normal butane, normal pentane and normal hexane. Three reactions promote the production of normal paraffin-iso-paraffin disproportionation reactions, reverse isomerization of iso-paraffins, and paraffin hydrocracking reactions.

Cracking of some of the paraffins can occur in the single isomerization unit 60' to produce C4− paraffins. Moreover, the conversion of isobutane, isopentane and/or isohexane increases significantly via disproportionation reactions due to the fact that the non-normal, non-cyclic paraffin rich stream in the intermediate raffinate overhead line 56' are passed into the single isomerization unit 60' lean in cyclic C6 hydrocarbons. It is believed that the paraffin disproportionation reactions occur by the combination of two iso-paraffins followed by scission into one lighter hydrocarbon and one heavier hydrocarbon. For example, two isopentanes can combine and form an isobutane and an isohexane in the presence of hydrogen. The isobutanes can further react via disproportionation to form a propanes and isopentanes. A significant portion of the produced isobutanes also converts to normal butanes via isomerization reactions in the isomerization zone. Production of normal propane and butane via disproportionation and isomerization reactions occurs with low production of low-value undesired methane as a cracked product. Thus, there is an increase in the overall yield of the normal paraffins in the single isomerization unit 60'.

In the single isomerization unit 60', hydrocracking of the isopentane and/or isohexane occurs to produce methane, ethane, propane, and isobutane. The isobutane can further react via disproportionation reactions and/or isomerization to further produce normal paraffins.

The single isomerization catalyst is capable of isomerizing all of isobutane, isopentane and isohexane to normal hydrocarbons. The isomerization catalyst in the single isomerization unit 60' may include chlorided alumina, sulfated zirconia, tungstated zirconia or zeolite-containing isomerization catalysts. The isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the single isomerization unit 60'. If chlorided alumina catalyst is used as the isomerization catalyst, a chloriding agent in line 63 will be added to the higher isomerization feed stream 61.

The higher isomerization process conditions in the single isomerization unit 60' include an average reactor temperature usually ranging from about 1800 to about 210° C. Reactor operating pressures generally range from about 250 to 500 psig. Liquid hourly space velocities (LHSV) range from about 3 to about 12 volumes of hydrocarbon feed per hour per volume of catalyst. Hydrogen is admixed with or remains with the higher isomerization feed to the higher isomerization unit to provide a mole ratio of hydrogen to hydrocarbon feed of from about 0.6 to 2.3. The hydrogen may be supplied totally from outside the process or supplemented by hydrogen recycled to the feed after separation from higher isomerization reactor effluent.

Contacting within the higher isomerization unit 90 may be effected using the higher isomerization catalyst in a fixed-bed system, a moving-bed system, a fluidized-bed system, or in a batch-type operation. The reactants may be contacted with the bed of higher isomerization catalyst particles in upward, downward, or radial-flow fashion. The reactants may be in the liquid phase, a mixed liquid-vapor phase, or a vapor phase when contacted with the higher isomerization catalyst particles, with a mixed phase or vapor phase being preferred. The higher isomerization unit 90 may be in a single reactor 96 or in two or more separate higher isomerization reactors 96 and 98 with suitable means therebetween to ensure that the desired isomerization temperature is maintained at the entrance to each reactor.

The reactions in the single isomerization unit 60' generate an exotherm across the reactors so the single isomerization effluent streams need to be cooled between reactors. For example, a first single isomerate stream from a first isomerization reactor 67 may be heat exchanged with the single isomerization feed stream in the single isomerization feed line 61 comprising the non-normal, non-cyclic paraffin rich stream mixed with hydrogen to cool the single isomerate and heat the single isomerization feed stream. Moreover, a second single isomerate stream from a second single isomerization reactor 68 may be heat exchanged with the single isomerization feed stream comprising the non-normal, non-cyclic paraffin rich stream mixed with hydrogen upstream of the heat exchange with the first single isomerate steam to cool the single isomerate stream and heat the single isomerization feed stream. Additionally, a third isomerate stream from the third isomerization reactor 69 may be heat exchanged with the single isomerization feed stream comprising non-normal, non-cyclic paraffin rich stream mixed with hydrogen upstream of the heat exchange with the second single isomerate stream to cool the single isomerate and heat the single isomerization feed stream. Since hydrocracking reactions are accompanied by hydrogenation reactions that are very exothermic, two to five single isomerization reactors in sequence enable improved control of individual reactor temperatures and partial catalyst replacement without a process shutdown. A single isomerization effluent stream comprising an increased concentration of normal paraffins exits the last single isomerization reactor 69 in the single isomerization unit 60' in a single isomerization effluent line 65.

The single isomerization effluent stream in the single isomerization effluent line 65 may be separated in a depropanizer 70 and further processed as explained with regard to FIG. 1.

The following Examples demonstrate the advantages of the present invention over the prior art of U.S. Pat. No. 9,302,958.

A chlorided-alumina catalyst that contained Pt was loaded and operated in a pilot plant with isopentane and isohexane rich feeds. The feeds contained 0.0-0.1 wt % C6 cyclics and are classified as C6 cyclic lean feeds. There were no C3 or C4 components in the feeds. Table 1 shows the composition of the feeds that were used in the testing.

TABLE 1

Composition of feeds tested in pilot plant.

|  | New Data | REFERENCE US9302958 FEED | US9302958 |
|---|---|---|---|
| COMPONENTS | FEED1 wt % | FEED2 wt % | FEED3 wt % |
| iC4 | 0.0 | 0.0 | 0.0 |
| nC4 | 0.0 | 0.0 | 0.0 |
| iC5 | 50.1 | 56.1 | 55.5 |
| nC5 | 1.7 | 1.8 | 1.9 |
| iC6 | 45.1 | 39.4 | 41.9 |
| nC6 | 1.3 | 1.1 | 0.5 |
| CP | 1.7 | 1.5 | 0.0 |
| C6 Cyclics | 0.1 | 0.0 | 0.0 |
| C7+ | 0.0 | 0.0 | 0.2 |
| Sum | 100.0 | 100.0 | 100.0 |

Table 2 shows the process conditions and product compositions that demonstrate the prior art. Products A, B, D, E and F show reverse isomerization reactions occurred forming n-pentane and n-hexane and some disproportionation reactions occurred forming propane and isobutane. The isobutane isomerized forming n-butane. The C4 isomerization reactions did not reach equilibrium since the measured nC4/(nC4+iC4) ratios were below the calculated equilibrium values for each condition. The hydrocracking reactions were minimal based on the relatively small methane and ethane concentrations in the products. Furthermore, Products D, E and F contained C7 components made via the disproportionation reaction 2iC6→iC5+iC7 demonstrating low hydrocracking of the heavier C7 species.

Product C, as reported in the art, was run at a high H2/HC ratio and showed that some hydrocracking reactions occurred as demonstrated by the formation of methane (1.5 wt %) and ethane (2.0 wt %). These conditions were considered unfavored due to a reduced normal paraffin/methane selectivity ratio of 24.

Table 3 shows the process conditions and product compositions G, H and I that demonstrate the invention. It is evident in the product compositions that isomerization, disproportionation and hydrocracking reaction are occurring. The hydrocracking reactions are evident by increased methane and ethane production, significant reduction of the C5 and C6 components from feed to product, and the disappearance of most the C7 components made by disproportionation reactions.

Figure 3:
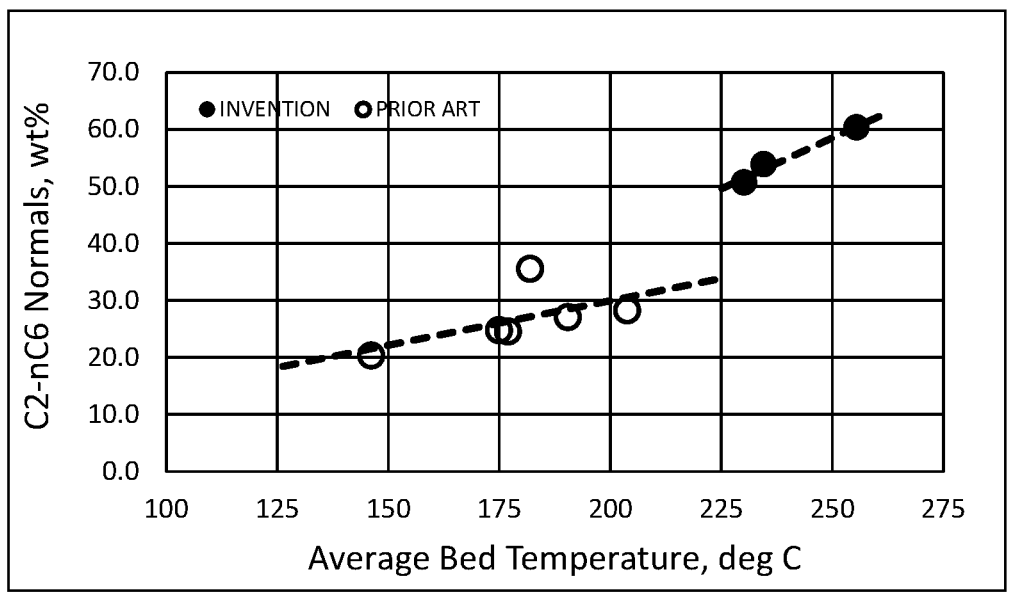
FIG. 3. Shows a graph of normal paraffin product versus temperature.
Figure 4:
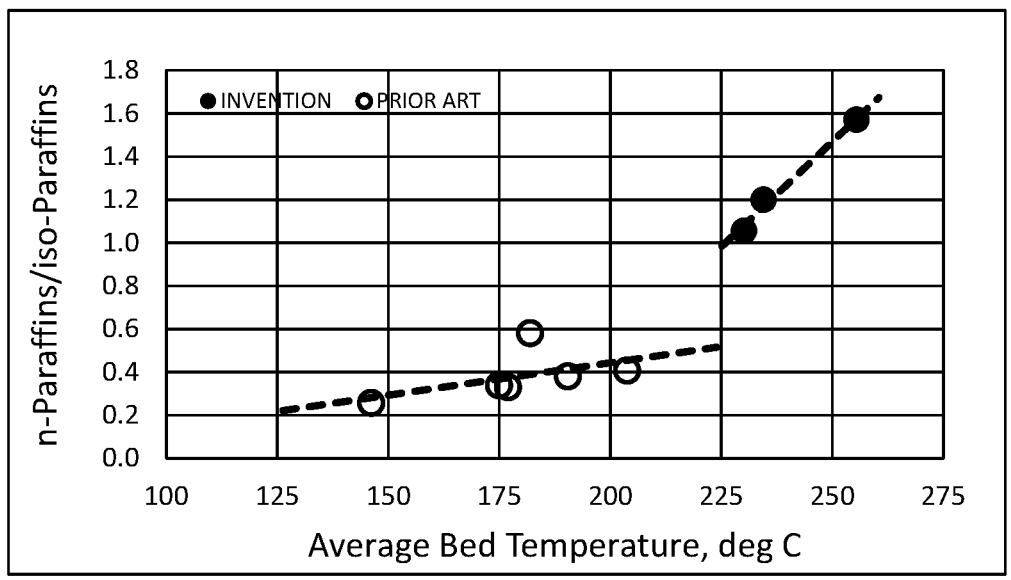
FIG. 4 shows the ratio of normal/iso paraffins versus temperature.
Figure 5:
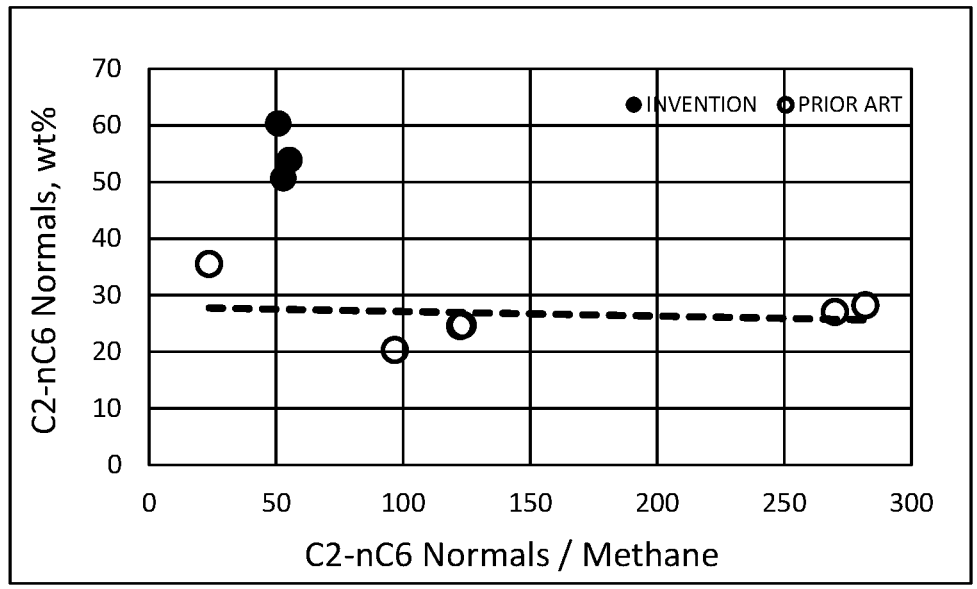
FIG. 5 shows the normal paraffin product/methane versus n-paraffin.
Figure 6:
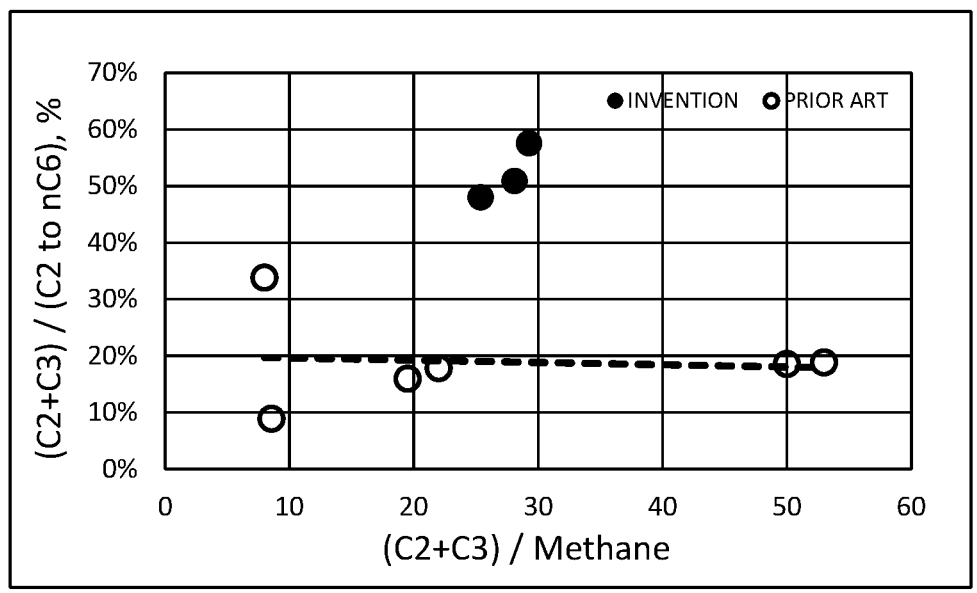
FIG. 6 shows the percent normal paraffins vs the ratio of C2 and C3 to C1.
Figure 7:
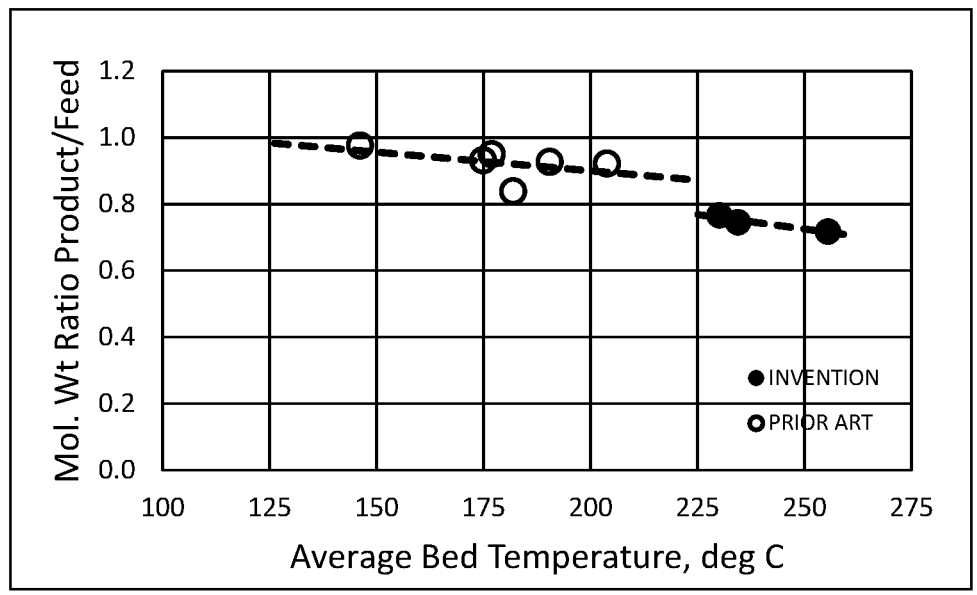
FIG. 7 shows the ratio of product molecular weight to feed.

FIGS. 3 and 4 shows that the invention provides a surprising and unexpected sharp increase in the desired amount of C2 to nC6 normal paraffins in the product and a sharp increase in the product normal/iso paraffin ratio. FIG. 3 shows that the invention provides high yields of C2 to nC6 normal paraffins while maintaining a normal-paraffin/C1 selectivity ratio of about 50. It is evident that the invention provides higher yields of normal paraffin products at a given n-paraffin/methane selectivity compared to the prior art. FIG. 4 shows a product normal/iso paraffin ratio versus the average reactor temperature with the invention showing a higher ratio achieved at higher temperatures than in the prior art. Furthermore, for the invention, the C4 isomerization reactions achieved equilibrium as demonstrated by the measured nC4/(iC4+nC4) ratios matching the equilibrium ratios. FIG. 5 shows a product of normal paraffins versus normal paraffin/methane selectivity ratio with a significant increase shown in the percentage of normal paraffins produced. FIG. 6 shows the percent of normal paraffins produced versus C2 plus C3/C1 selectivity ratio. FIG. 7 shows a ratio of product of molecular weight to feed.

In this Example 1, the desired increase in production of normal paraffins is attained by operating at temperatures greater than about 204° C., at elevated liquid hourly space velocities of over about 2.0 h−1, and H2/HC inlet ratios of greater than about 0.32 mole ratio. The examples show good operation of the invention at LHSV's over about 4 h−1, temperatures over about 225° C., and H2/HC inlet mole ratios greater than about 0.5. The total pressure at the reactor inlet ranges between about 450 to 650 psig. It is thought that the conditions of the invention provide a controlled level of hydrocracking reactions that lead to significantly higher normal paraffin production with limited production of undesired methane.

TABLE 2

Pilot plant data demonstrating prior art.

| CONDITIONS | PRIOR ART | | | | | |
|---|---|---|---|---|---|---|
| Average Temp, C. | 146 | 177 | 182 | 175 | 191 | 204 |
| Pressure, psig | 448 | 450 | 450 | 450 | 449 | 450 |
| LHSV, h-1 | 1.5 | 2.0 | 2.0 | 2.0 | 2.0 | 2.0 |
| H2/HC inlet, mole | 0.21 | 0.32 | 1.07 | 0.30 | 0.25 | 0.20 |
| Feed Used in Test | FEED 1 | FEED 2 | FEED 2 | FEED 3 | FEED 3 | FEED 3 |

| | PRODUCT | | | | | |
|---|---|---|---|---|---|---|
| COMPONENTS | A wt % | B wt % | C wt % | D wt % | E wt % | F wt % |
| H2 | 0.3 | 0.5 | 1.8 | 0.5 | 0.3 | 0.1 |
| C1 | 0.2 | 0.2 | 1.5 | 0.2 | 0.1 | 0.1 |

TABLE 2-continued

Pilot plant data demonstrating prior art.

| | | | | | | |
|---|---|---|---|---|---|---|
| C2 | 0.3 | 0.3 | 2.0 | 0.2 | 0.2 | 0.1 |
| C3 | 1.5 | 3.6 | 10.0 | 4.2 | 4.8 | 5.2 |
| iC4 | 4.2 | 9.2 | 17.8 | 13.1 | 14.7 | 15.6 |
| nC4 | 1.6 | 4.5 | 12.1 | 5.6 | 7.1 | 7.9 |
| iC5 | 35.9 | 34.1 | 25.8 | 30.9 | 29.5 | 28.2 |
| nC5 | 11.5 | 11.5 | 8.8 | 10.5 | 10.7 | 10.8 |
| iC6 | 39.1 | 31.4 | 17.7 | 29.1 | 26.9 | 25.6 |
| nC6 | 5.4 | 4.6 | 2.6 | 4.2 | 4.2 | 4.2 |
| CP | 0.0 | 0.0 | 0.0 | 0.0 | 0.1 | 0.1 |
| C6 Cyclics | 0.0 | 0.0 | 0.0 | 0.0 | 0.0 | 0.0 |
| C7+ | 0.0 | 0.2 | 0.0 | 1.4 | 1.6 | 2.1 |
| Sum | 100.0 | 100.1 | 100.1 | 99.9 | 100.2 | 100.0 |

PRODUCT CONVERSIONS & COMPOSITIONS

| | | | | | | |
|---|---|---|---|---|---|---|
| C2 to nC6, wt % | 20.3 | 24.5 | 35.5 | 24.7 | 27.0 | 28.2 |
| n-Paraffin/iso-Paraffin | 0.26 | 0.33 | 0.58 | 0.34 | 0.38 | 0.41 |
| Normal-Paraffin/C1 | 97 | 123 | 24 | 124 | 270 | 282 |
| (C2 + C3)/(C2 to nC6), % | 8.8% | 15.9% | 33.8% | 17.8% | 18.5% | 18.8% |
| (C2 + C3)/C1 | 8.6 | 19.5 | 8.0 | 22.0 | 50.0 | 53.0 |
| Mol. Wt Ratio | 0.98 | 0.95 | 0.84 | 0.93 | 0.93 | 0.92 |

TABLE 3

Pilot plant data demonstrating the invention.

| CONDITIONS | INVENTION | | |
|---|---|---|---|
| Average Temp, C. | 230 | 235 | 256 |
| Pressure, psig | 447 | 546 | 643 |
| LHSV, h-1 | 4.2 | 4.3 | 7.5 |
| H2/HC inlet, mole | 0.54 | 0.52 | 0.55 |
| Feed Used in Test | FEED 1 | FEED 1 | FEED 1 |

PRODUCT

| COMPONENTS | G wt % | H wt % | I wt % |
|---|---|---|---|
| H2 | 0.3 | 0.1 | 0.0 |
| C1 | 1.0 | 1.0 | 1.2 |
| C2 | 1.4 | 1.4 | 1.8 |
| C3 | 22.9 | 26.0 | 32.9 |
| iC4 | 22.1 | 24.5 | 22.3 |
| nC4 | 18.0 | 19.9 | 19.9 |
| iC5 | 17.1 | 14.1 | 11.7 |
| nC5 | 6.8 | 5.5 | 4.9 |
| iC6 | 8.8 | 6.3 | 4.4 |
| nC6 | 1.6 | 1.1 | 0.8 |
| CP | 0.0 | 0.0 | 0.0 |
| C6 Cyclics | 0.0 | 0.0 | 0.0 |
| C7+ | 0.1 | 0.1 | 0.1 |
| Sum | 100.0 | 100.0 | 100.0 |

PRODUCT CONVERSIONS & COMPOSITIONS

| | | | |
|---|---|---|---|
| C2 to nC6, wt % | 50.7 | 53.9 | 60.3 |
| n-Paraffin/iso-Paraffin | 1.06 | 1.20 | 1.57 |
| Normal-Paraffin/C1 | 53 | 55 | 51 |
| (C2 + C3)/(C2 to nC6), % | 48.0% | 50.9% | 57.5% |
| (C2 + C3)/C1 | 25.4 | 28.1 | 29.3 |
| Mol. Wt Ratio | 0.77 | 0.74 | 0.72 |

Example 2

A sulfated zirconia catalyst that contained Pt was loaded and operated in a pilot plant with two different feed (a) iso C4, iso C5 and iso C6s rich feed (b) feed with rich in iso C4, iso C5, iso C6s and rings (C5, C6, C7, C8s)~8.9 wt % and C7+~5 wt %. There were no C2 or C3 components in the feeds. Table 4 shows the composition of the feeds that were used in the testing.

TABLE 4

Composition of feeds tested in pilot plant.

| | FEED1 US9302960 B2 Prior Art | FEED2 Invention | FEED3 Invention |
|---|---|---|---|
| iC4 | | 38 | 29. |
| nC4 | | 0.1 | 4.4 |
| iC5 | 96.8 | 34.4 | 28.5 |
| nC5 | 3.2 | 0.7 | 0.6 |
| iC6 | | 26.0 | 23.7 |
| nC6 | | 0.7 | 0.6 |
| CP | | 0 | 2.2 |
| C6 Cyclics | | 0.1 | 5.7 |
| C7+ | | 0.01 | 5.2 |

Figure 8:
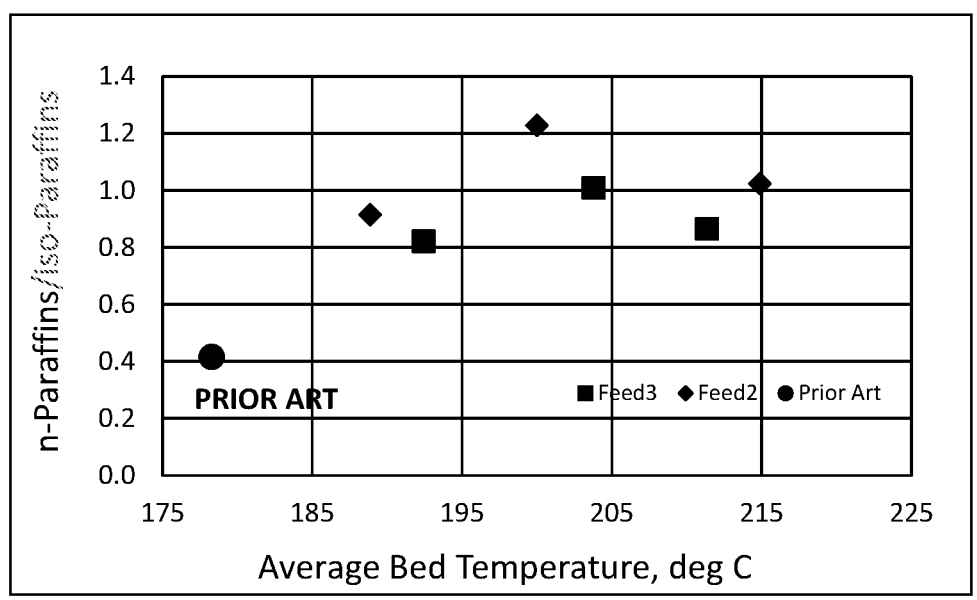
FIG. 8 shows product normal/iso paraffin ratio vs. average reactor temperature for a sulfated zirconia catalyst.
Figure 9:
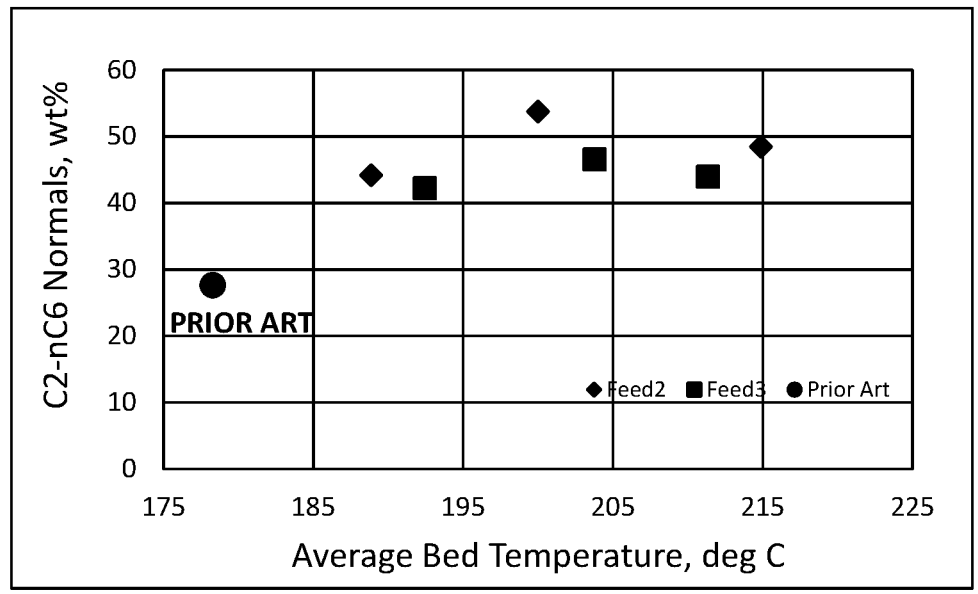
FIG. 9 shows product normal paraffins vs. average reactor temperature.
Figure 10:
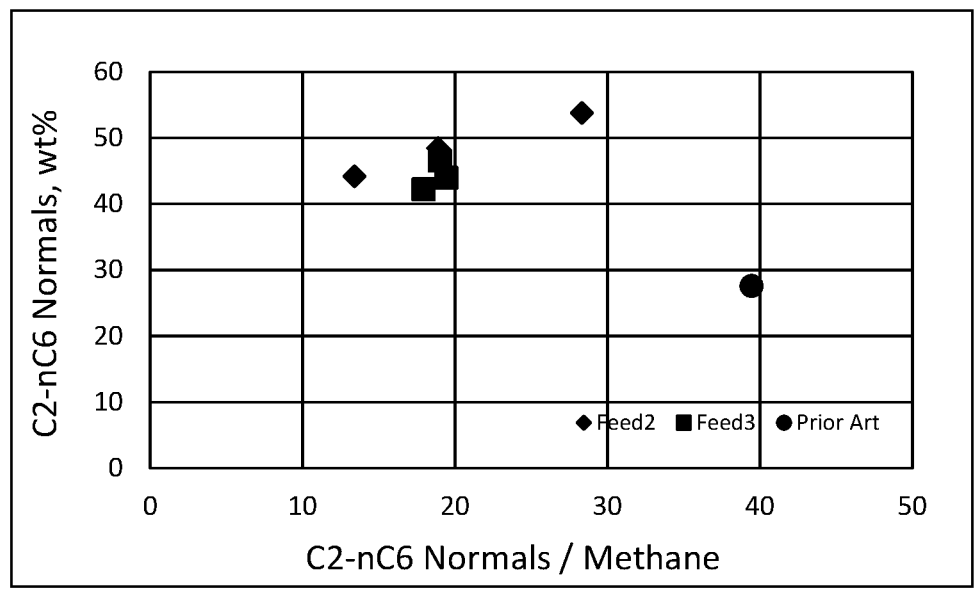
FIG. 10 shows product normal paraffins vs. normal paraffin/C1 selectivity ratio.
Figure 11:
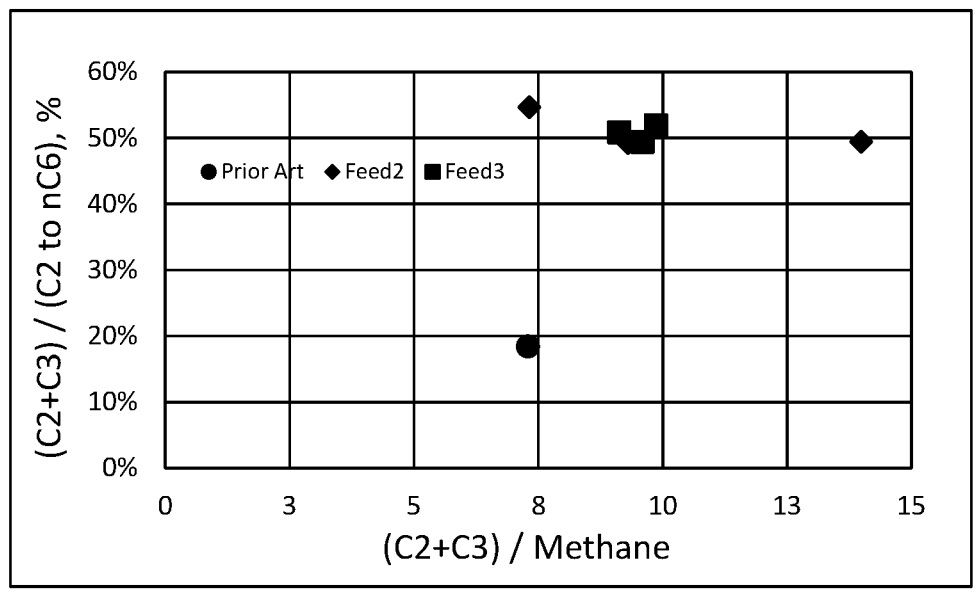
FIG. 11 shows percent $C_2+C_3$ normal paraffins produced vs. $(C_2+C_3)/C_1$ selectivity ratio.
Figure 12:
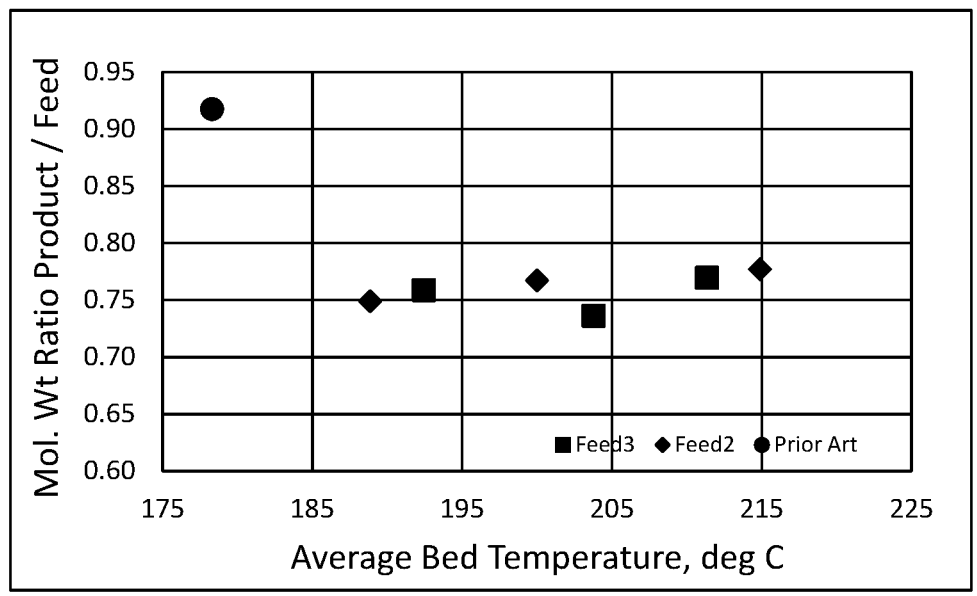
FIG. 12 shows ratio of product molecular weight to feed

FIGS. 8-12 show comparisons of feeds both with and without cyclic paraffins in comparison with the prior art. FIG. 8 shows that the invention provides increase in the desired amount of C2 to nC6 normal paraffins in the product for feed with and without rings. Specifically FIG. 8 shows product normal/iso paraffin ratio vs average reactor temperature. FIG. 9 shows that the invention provides high yields of C2 to nC6 normal paraffins while maintaining a similar normal-paraffin/C1 selectivity ratio as prior art. FIG. 10 shows that the invention provides a greater amount of normal paraffins although with a lower (C2+C3)/methane selectivity ratio as compared to the prior art. FIG. 11 shows that the invention provides a greater percentage of desired C2+C3 paraffins at a given (C2+C3)/methane selectivity ratio as compared to the prior art. FIG. 12 shows the ratio of product molecular weight to feed.

The invention is attained by operating at temperatures greater than about 180° C., pressure in the range of 250-500 psig, H2/HC~0.6-2.3 mol/mol and LHSV 3-12 l/h.

The Figures show the molecular weight reduction of feed to product. Molecular weight product ratios of 0.7-0.8 were obtained for FEED-2 and FEED-3 and lower compared with FEED-1 (prior art). The reduction in molecular weight is combination of hydrocracking, disproportionation and reverse isomerization for FEED-2 and additionally ring saturation, ring isomerization, ring opening for FEED-3.

Tables 5 and 6 shows the process conditions and product compositions that demonstrate the Invention-Feed 2 and Invention-Feed 3. It is evident in the product compositions that isomerization, disproportionation and hydrocracking reaction are occurring. The hydrocracking reactions are evident by increased methane and ethane production, significant reduction of the C5 and C6 components from feed to product, and the disappearance of most of the C7+ components from feed and made by disproportionation reactions.

Products B, C, D, E, F, and G show reverse isomerization reactions occurred forming n-pentane and n-hexane and some disproportionation reactions occurred forming propane and isobutane. The isobutane isomerized forming n-butane. The C4 isomerization reactions did not reach equilibrium since the measured nC4/(nC4+iC4) ratios were below the calculated equilibrium values for each condition. The hydrocracking reactions were moderate based on the ethane and ethane concentrations in the products.

A first embodiment of the invention is a process for increasing the concentration of normal paraffins in a feed stream comprising separating a naphtha feed stream into a normal paraffin stream and a non-normal paraffin stream wherein the non-normal paraffin stream further comprises about 1-30 wt % cyclic hydrocarbons; sending the non-normal paraffin stream to be isomerized reacted over an isomerization catalyst in an isomerization zone at a temperature in a range from about 180° C. to 260° C. to convert non-normal paraffins to normal paraffins and produce an effluent stream. An embodiment of the invention is one, any or all of prior embodiments in this paragraph up through the first embodiment in this paragraph wherein the temperature is a range from about 200 to 260° C. An embodiment of the invention is one, any or all of prior embodiments in this paragraph up through the first embodiment in this paragraph wherein the non-normal paraffin stream is isomerized at a liquid space velocity of about 1.5 to 5.0 l/h and a ratio of hydrogen/hydrocarbon of about 0.5 to 2.5 at an inlet. An embodiment of the invention is one, any or all of prior embodiments in this paragraph up through the first embodiment in this paragraph wherein the isomerization effluent stream comprises a normal paraffin/methane selectivity ratio of about 40-55. An embodiment of the invention is one, any or all of prior embodiments in this paragraph up through the first embodiment in this paragraph wherein the isomerization zone maintains a pressure in the range of about 250-500 psig. An embodiment of the invention is one, any or all of prior embodiments in this paragraph up through the first

TABLE 5

Pilot plant data demonstrating prior art and Invention-Feed 2 and 3

|  | PRIOR ART | INVENTION | | | | | |
| --- | --- | --- | --- | --- | --- | --- | --- |
| Average Temp, C. | 178.3 | 188.9 | 200.0 | 214.9 | 192.4 | 211.3 | 203.8 |
| Pressure, psig | 449 | 448.4 | 248.1 | 498.0 | 448.1 | 497.8 | 464.5 |
| LHSV, h-1 | 7.7 | 3.86 | 3.01 | 11.97 | 3.75 | 7.06 | 3.75 |
| H2/HC inlet, mole | 2.1 | 1.89 | 0.60 | 1.00 | 2.00 | 1.60 | 2.30 |
| Feed Used in Test | FEED1 | FEED2 | FEED2 | FEED2 | FEED3 | FEED3 | FEED3 |
| Product Components | Product | Product | Product | Product | Product | Product | Product |
| Components, wt % | A | B | C | D | E | F | G |
| H2 | 5.2 | 4.2 | 0.6 | 1.7 | 3.9 | 2.9 | 4.8 |
| C1 | 0.7 | 3.3 | 1.9 | 2.6 | 2.4 | 2.3 | 2.5 |
| C2 | 2 | 7.8 | 4.1 | 5.8 | 6.2 | 5.5 | 6.8 |
| C3 | 3.1 | 16.4 | 22.4 | 18.0 | 15.3 | 16.3 | 17.4 |
| iC4 | 5.2 | 34.1 | 36.7 | 34.0 | 32.1 | 31.6 | 29.6 |
| nC4 | 2.9 | 15.8 | 25.0 | 20.2 | 15.2 | 16.3 | 17.3 |
| iC5 | 55.8 | 11.8 | 6.1 | 10.8 | 14.5 | 14.0 | 13.1 |
| nC5 | 18.8 | 3.9 | 2.1 | 4.0 | 4.8 | 5.1 | 4.6 |
| iC6 | 5.6 | 2.5 | 0.9 | 2.5 | 4.8 | 5.2 | 3.5 |
| nC6 | 0.8 | 0.3 | 0.1 | 0.4 | 0.7 | 0.8 | 0.5 |
| CP | 0.2 | 0.0 | 0.0 | 0.0 | 0.0 | 0.0 | 0.0 |
| C6 Cyclics | 0 | 0.0 | 0.0 | 0.0 | 0.0 | 0.0 | 0.0 |
| C7+ | 0 | 0.0 | 0.0 | 0.0 | 0.0 | 0.0 | 0.0 |
| Sum | 100 | 100 | 100 | 100 | 100 | 100 | 100 |
| C2 to nC6, wt % | 27.6 | 44.2 | 53.8 | 48.4 | 42.3 | 44.0 | 46.6 |
| n-Paraffin/iso-Paraffin | 0.4 | 0.9 | 1.2 | 1.0 | 0.8 | 0.9 | 1.0 |
| Normal-Paraffin/C1 | 39.4 | 13.4 | 28.3 | 18.9 | 17.9 | 19.4 | 19.0 |
| (C2 + C3)/(C2 to nC6), % | 0.2 | 0.5 | 0.5 | 0.5 | 0.5 | 0.5 | 0.5 |
| (C2 + C3)/C1 | 7.3 | 7.3 | 14.0 | 9.3 | 9.1 | 9.6 | 9.9 |
| Mol. Wt Ratio | 0.92 | 0.75 | 0.77 | 0.78 | 0.76 | 0.77 | 0.74 |

Specific Embodiments

While the following is described in conjunction with specific embodiments, it will be understood that this description is intended to illustrate and not limit the scope of the preceding description and the appended claims.

embodiment in this paragraph wherein the isomerization zone produces about 30-65 wt % normal paraffins. An embodiment of the invention is one, any or all of prior embodiments in this paragraph up through the first embodiment in this paragraph wherein the isomerization zone produces about 30-60 wt % C2-C3 normal paraffins. An embodiment of the invention is one, any or all of prior embodiments in this paragraph up through the first embodiment in this paragraph wherein the effluent stream has an effluent molecular weight/feed molecular weight ratio of about 0.70 to 0.80 wherein the feed is the non-normal paraffin stream. An embodiment of the invention is one, any or all of prior embodiments in this paragraph up through the first embodiment in this paragraph wherein the effluent stream has a normal paraffin/iso paraffin ratio of about 0.8-2.0. An embodiment of the invention is one, any or all of prior embodiments in this paragraph up through the first embodiment in this paragraph wherein the effluent stream has a light paraffin (C2-C3) ratio to methane of about 50-60%.

A second embodiment of the invention is a process for increasing the concentration of normal paraffins in a feed stream comprising separating a naphtha feed stream into a normal paraffin stream and a non-normal paraffin stream comprising less than about 0.5 wt % cyclic hydrocarbons; in an isomerization zone isomerizing an isomerization feed stream taken from the non-normal paraffin stream over an isomerization catalyst at a temperature in a range from about 225 to 260° C. to convert non-normal paraffins to normal paraffins and produce an isomerization effluent stream; separating the isomerization effluent stream into a propane stream and a C4+ hydrocarbon stream wherein the isomerization effluent stream has a normal/iso ratio of about 1-1.7. An embodiment of the invention is one, any or all of prior embodiments in this paragraph up through the second embodiment in this paragraph wherein the C4+ hydrocarbon stream is a C4-C6 hydrocarbon stream. An embodiment of the invention is one, any or all of prior embodiments in this paragraph up through the second embodiment in this paragraph wherein the isomerization effluent stream comprises a normal paraffin/methane selectivity ratio of about 40-55. An embodiment of the invention is one, any or all of prior embodiments in this paragraph up through the second embodiment in this paragraph wherein the isomerization zone maintains a pressure in the range of 450-650 psig. An embodiment of the invention is one, any or all of prior embodiments in this paragraph up through the second embodiment in this paragraph wherein the isomerization zone produces about 30-65 wt % normal paraffins. An embodiment of the invention is one, any or all of prior embodiments in this paragraph up through the second embodiment in this paragraph wherein the effluent stream has a light paraffins (C2-C3) over methane selectivity of about 50-60%. An embodiment of the invention is one, any or all of prior embodiments in this paragraph up through the second embodiment in this paragraph wherein the isomerization effluent stream has a molecular weight ratio to the isomerization feed stream of about 0.70 to 0.80. An embodiment of the invention is one, any or all of prior embodiments in this paragraph up through the second embodiment in this paragraph wherein the process is at a LHSV of about 4-7.5. An embodiment of the invention is one, any or all of prior embodiments in this paragraph up through the second embodiment in this paragraph wherein the isomerization feed stream has an inlet mole ratio of H2/hydrocarbon of about 0.5 to 0.6.

A third embodiment of the invention is a process for treating a naphtha feed stream comprising separating a naphtha feed stream into a normal paraffin stream and a non-normal paraffin stream comprising less than about 0.5 wt % cyclic hydrocarbons; and; in an isomerization zone isomerizing an isomerization feed stream taken from the non-normal paraffin stream over a chlorided alumina catalyst at a temperature in a range from about 225 to 260° C. to convert non-normal paraffins to normal paraffins and produce an isomerization effluent stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for increasing the concentration of normal paraffins in a feed stream comprising:
    separating a naphtha feed stream into a normal paraffin stream and a non-normal paraffin stream comprising $C_5$ and C6 non-normal paraffins and less than about 0.5 wt % cyclic hydrocarbons;
    isomerizing the non-normal paraffin stream over an isomerization catalyst at a temperature in a range from about 225 to 260° C. to produce an isomerization effluent stream;
    separating said isomerization effluent stream into a propane stream and a C4+ hydrocarbon stream wherein said isomerization effluent stream has a normal/iso ratio of about 1-1.7; and
    recycling said C4+ hydrocarbon stream to said naphtha feed stream for separation of the normal paraffins from the non-normal paraffins,
    wherein said isomerization effluent stream comprises $C_2$-$C_6$ normal paraffins to methane selectivity ratio of about 40-55 based on weight, wherein the isomerization is conducted at a liquid hourly space velocity (LHSV) of about 4 to 7.5 $h^{-1}$, and wherein said isomerization feed stream has an inlet mole ratio of $H_2$/hydrocarbon of about 0.5 to 0.6.

2. The process of claim 1 wherein said C4+ hydrocarbon stream is a C4-C6 hydrocarbon stream.

3. The process of claim 1 wherein said isomerization zone maintains a pressure in the range of 450-650 psig.

4. The process of claim 1 wherein said isomerization zone produces about 30-65 Wt % $C_2$-$C_6$ normal paraffins.

5. The process of claim 3 wherein said effluent stream has a light paraffins (C2-C3) to $C_2$-$C_6$ normal paraffins selectivity of about 50-60% based on weight.

6. The process of claim 1 wherein a molecular weight ratio of said isomerization effluent stream to said isomerization feed stream is about 0.70 to 0.80.

7. A process for treating a naphtha feed stream comprising:
    separating a naphtha feed stream into a normal paraffin stream and a non-normal paraffin stream comprising $C_5$ and $C_6$ non-normal paraffins and less than about 0.5 wt % cyclic hydrocarbons;
    isomerizing the non-normal paraffin stream over a chlorided alumina catalyst at a temperature in a range from about 225 to 260° C. to produce an isomerization effluent stream;
    separating said isomerization effluent stream with a depropanizer column into a depropanizer overhead stream comprising propane and a depropanizer bottoms stream comprising C4+ paraffins; and recycling said depropanizer bottoms stream comprising C4+ paraffins to said naphtha feed stream for separation of the normal paraffins from the non-normal paraffins, wherein said isomerization effluent stream comprises a $C_2$-$C_6$ normal paraffins to methane selectivity ratio of about 40-55 based on weight, wherein the isomerization is conducted at a liquid hourly space velocity (LHSV) of about 4 to 7.5 $h^{-1}$, and wherein said isomerization feed stream has an inlet mole ratio of $H_2$/hydrocarbon of about 0.5 to 0.6.

* * * * *